US011191249B2

(12) United States Patent
Spangenberg et al.

(10) Patent No.: US 11,191,249 B2
(45) Date of Patent: Dec. 7, 2021

(54) BRACHIARIA ENDOPHYTES AND RELATED METHODS

(71) Applicant: Agriculture Victoria Services PTY LTD, Attwood (AU)

(72) Inventors: German Carlos Spangenberg, Bundoora (AU); Kathryn Michaela Guthridge, Glenroy (AU); Ross Mann, Wendouree (AU); Timothy Ivor Sawbridge, Coburg (AU); Inoka Kumari Hettiarachchige, Kingsbury (AU); Piyumi Niroshini Ekanayake, Mernda (AU); Natasha Denise Brohier, Southbank (AU); Simone Jane Rochfort, Reservoir (AU); Jacqueline Edwards, Brunswick (AU)

(73) Assignee: Agriculture Victoria Services PTY LTD, Bundoora (AU)

( * ) Notice: Subject to any disclaimer, the term of this patent is extended or adjusted under 35 U.S.C. 154(b) by 171 days.

(21) Appl. No.: 15/762,988

(22) PCT Filed: Sep. 23, 2016

(86) PCT No.: PCT/AU2016/050887
§ 371 (c)(1),
(2) Date: Mar. 23, 2018

(87) PCT Pub. No.: WO2017/049352
PCT Pub. Date: Mar. 30, 2017

(65) Prior Publication Data
US 2018/0213797 A1 Aug. 2, 2018

(30) Foreign Application Priority Data

Sep. 24, 2015 (AU) ............................. 2015903909
Aug. 12, 2016 (AU) ............................. 2016903174

(51) Int. Cl.
| | | |
|---|---|---|
| *C12N 15/82* | (2006.01) | |
| *A01H 17/00* | (2006.01) | |
| *C12Q 1/689* | (2018.01) | |
| *C12Q 1/6895* | (2018.01) | |
| *C12P 5/00* | (2006.01) | |
| *C12N 1/14* | (2006.01) | |
| *C12N 1/20* | (2006.01) | |
| *C07D 493/00* | (2006.01) | |
| *C07D 493/08* | (2006.01) | |
| *A01N 63/30* | (2020.01) | |
| *C12N 15/10* | (2006.01) | |
| *C12P 17/06* | (2006.01) | |
| *C12R 1/01* | (2006.01) | |
| *C12R 1/645* | (2006.01) | |

(52) U.S. Cl.
CPC ............ *A01H 17/00* (2013.01); *A01N 63/30* (2020.01); *C07D 493/00* (2013.01); *C07D 493/08* (2013.01); *C12N 1/14* (2013.01); *C12N 1/145* (2021.05); *C12N 1/20* (2013.01); *C12N 1/205* (2021.05); *C12N 15/1003* (2013.01); *C12P 5/007* (2013.01); *C12P 17/06* (2013.01); *C12Q 1/689* (2013.01); *C12Q 1/6895* (2013.01); *C12Q 2600/156* (2013.01); *C12R 2001/01* (2021.05); *C12R 2001/645* (2021.05)

(58) Field of Classification Search
None
See application file for complete search history.

(56) References Cited

FOREIGN PATENT DOCUMENTS

| | | | |
|---|---|---|---|
| JP | 2010-248088 A | 11/2010 | |
| WO | 2012/174585 A1 | 12/2012 | |
| WO | WO-2012174585 A1 * | 12/2012 | ...... C12Y 102/01009 |
| WO | 2013/177615 A1 | 12/2013 | |
| WO | WO-2013177615 A1 * | 12/2013 | ............. A01H 17/00 |
| WO | 2014020141 A1 | 2/2014 | |
| WO | 2014094279 A1 | 6/2014 | |
| WO | 2014121302 A2 | 8/2014 | |
| WO | WO-2013177615 A9 * | 6/2017 | ............. A01H 17/00 |

OTHER PUBLICATIONS

Subbarao et al. (PNAS, 106:17302-17307, Published 2009).*
Kelemu et al. (Canadian Journal of Microbiology, 47:55-62, 2001).*
Porras-Alfaro et al. (Annu. Rev. Phytopathol. 49:291-315, 2011).*
Lundberg et al. (Nature, 488:86-90, 2012).*
Martin, K. et al. "Fungal-specific PCR primers developed for analysis of the ITS region of environmental DNA extracts" BMC Microbiology, 2005, pp. 1-11, vol. 5, No. 28.
Mcbain, A. et al. "Microbial Characterization of Biofilms in Domestic Drains and the Establishment of Stable Biofilm Microcosms" Applied and Environmental Microbiology, 2003, pp. 177-185, vol. 69, No. 1.
Subbarao, G.V. et al. "A bioluminescence assay to detect nitrification inhibitors released from plant roots: a case study with Brachiaria humidicola" Plant Soil, 2006, pp. 101-112, vol. 288.
Subbarao, G.V. et al. "Evidence for Biological nitrification inhibition in Brachiaria pastures" PNAS, 2009, p. 17302-17307, vol. 106, No. 41.
Wang, Y. et al. "Conservative Fragments in Bacterial 16S rRNA Genes and Primer Design for 16S Ribosomal DNA Amplicons in Metagenomic Studies", PLOS One, 2009, pp. 1-9, e7401, vol. 4, Issue 10.
White, T.J. et al. "Amplification and Direct Sequencing of Fingal Ribosomal RNA Genes for Phylogenetics" in PCR Protocols: A Guide to Methods and Applications, 1990, pp. 315-322, Academic Press.
De Boer, A. H. et al., "Fusicoccanes: diterpenes with surprising biological functions" Trends in Plant Science, 2012, pp. 360-368, vol. 17, No. 6.

(Continued)

*Primary Examiner* — Vinod Kumar
(74) *Attorney, Agent, or Firm* — Larson & Anderson, LLC

(57) ABSTRACT

The present invention relates to endophytes, in particular endophytes associated with plants of the *Brachiaria-Urochloa* species complex, plants infected with the endophytes, products produced by the endophytes, and related methods.

6 Claims, 12 Drawing Sheets

(56) References Cited

OTHER PUBLICATIONS

Ambrose, K.V. et al. "Counting Genes and Comprehending processes: How high-throughout sequencing is aiding in peicing together grass-endophytes symbiosis puzzle" Phytopathology; Abstracts Presented in at the APS Northeastern Division, Oct. 12-14, 2011, vol. 102, No. 1, Suppl. 1.

Herrera. J. et al. "Assessment of root-associated fungal communities colonizing two species of tropical grasses reveals incongruence to fungal communities of North American native grasses" Fungal Ecology, 2013, pp. 65-69, vol. 6, No. 1.

* cited by examiner

BRACHIARIA ENDOPHYTES AND RELATED METHODS

FIELD OF THE INVENTION

The present invention relates to endophytes, plants infected with endophytes, products produced by the endophytes and related methods.

BACKGROUND OF THE INVENTION

Microbes represent an invaluable source of novel genes and compounds that have the potential to be utilised in a range of industrial sectors. Scientific literature gives numerous accounts of microbes being the primary source of antibiotics, immune-suppressants, anticancer agents and cholesterol-lowering drugs, in addition to their use in environmental decontamination and in the production of food and cosmetics.

A relatively unexplored group of microbes known as endophytes, which reside in the tissues of living plants, offer a particularly diverse source of novel compounds and genes that may provide important benefits to society, and in particular, agriculture.

Endophytes often form mutualistic relationships with their hosts, with the endophyte conferring increased fitness to the host, often through the production of defence compounds. At the same time, the host plant offers the benefits of a protected environment and nutriment to the endophyte.

Other microbes, such as bacteria which can reside in the tissues of living plants, are also relatively unexplored in this setting. Plant-borne bacteria offer similar benefits.

The *Brachiaria-Urochloa* species complex is a component of the grass family Poaceae, with representatives distributed throughout tropical regions, particularly in Africa. Genetic diversity analysis based on internal transcribed spacer (ITS) nuclear ribosomal DNA sequence data indicates a strong affinity between *Urochloa* and *Brachiaria*, supporting morphological and anatomical studies that show a continuous gradation between these grass genera. Some *Brachiaria-Urochloa* species are economically significant tropical forage grasses that have been released as commercial cultivars and include *B. brizantha, B. decumbens, B. humidicola*, and *B. ruziziensis*, as well as corresponding interspecific and intraspecific hybrids.

Methods for the identification and characterization of novel endophytes and their deployment in *Brachiaria-Urochloa* plant improvement programs have been discussed in WO2012/174585, the disclosure of which is hereby incorporated herein in its entirety. Strains of endophytic fungi were isolated from *Brachiaria-Urochloa* species. These brachiaria fungal endophytes were genetically diverse. Some of these endophytes exhibited broad spectrum antifungal activity and may play a role in protecting *Brachiaria-Urochloa* from fungal pathogens, such as *Drechslera* spp., which cause leaf spots.

There remains a general lack of information and knowledge of the fungal endophytes of the *Brachiaria-Urochloa* species complex as well as of methods for the identification and characterisation of novel endophytes and their deployment in *Brachiaria-Urochloa* plant improvement programs.

There is also a general lack of information and knowledge of the bacterial endophytes of the *Brachiaria-Urochloa* species complex as well as of methods for the identification and characterisation of novel bacterial organisms and their deployment in *Brachiaria-Urochloa* plant improvement programs.

Furthermore, although widely used for pasture-based agriculture in tropical regions of South America, Asia and Australia, *Brachiaria-Urochloa* exhibits a number of shortcomings that constrain both its use and genetic enhancement.

Forage grasses, including *Brachiaria-Urochloa*, have also been recognised in recent years for implications in nitrogen pollution. A major concern of modern production in agriculture is the high level of nitrogen (N) pollution and low efficiency of N utilisation. N losses from denitrification results in environmental pollution and inefficient use of both soil N and applied N (as fertiliser).

Nitrification is carried out primarily by two groups of chemo-lithotrophic bacteria (*Nitrosomonas* sp. and *Nitrobacter* spp), ubiquitous components of the soil microbial population. For example, nitrifying soil bacteria, such as *Nitrosomonas* spp convert ammonium ($NH_4^+$) to nitrate ($NO_3^-$). Nitrate can also be converted to nitrous oxide ($N_2O$) gas. Inhibition of nitrification may keep N in soil for longer and improve nitrogen use efficiency (NUE).

A bioluminescence assay using a recombinant strain of *Nitrosomonas europaea* has been developed to detect nitrification inhibitors released from plant roots, making it possible to determine and compare the biological nitrification inhibition (BNI) capacity of different crops and pastures (Subbarao et al., 2006).

The concept of plants releasing inhibitory compounds that suppress soil nitrification has previously been suggested. Several researchers have observed a slow rate of nitrification in soils of certain tropical grassland and forest soils. BNI is the ability of certain plant species to release organic compounds from their roots that have a targeted suppressive effect on soil nitrifying bacteria (Subbarao et al., 2006 2009).

Brachialactone is the major nitrification inhibitor released from roots of *B. humidicola* (Subbarao et al. 2009). Brachialactone belongs to a group of diterpenes called Fusicoccanes. Fusicoccanes have been identified and isolated from a diverse range of plants, fungi and bacteria. Brachialactone has been shown to exhibit biocidal activity against *Nitrosomonas* spp (Subbarao et al. 2009). N is then available to plant, increasing pasture performance. Literature has suggested that this compound is produced by the plant in response to ammonium in the root environment (Subbarao et al. 2009).

It is an object of the present invention to overcome, or at least alleviate, one or more of the difficulties or deficiencies associated with the prior art.

SUMMARY OF THE INVENTION

In one aspect, the present invention provides a method for isolating, selecting and/or characterising an endophyte strain, said method including:
  providing samples of plant material from plant species of the *Brachiaria-Urochoa* species complex;
  subjecting said samples to metagenomic analysis;
  identifying bacterial and/or fungal operational taxonomic units (OTUs) in each *Brachiaria-Urochoa* plant species;
  comparing the OTUs present in each sample species to identify core, supplemental and/or unique microbiomes; and
  selecting endophyte strains representing a desired core, supplemental or unique microbiome.

By an endophyte strain is meant a bacterial or fungal strain that is closely associated with a plant, preferably a plant of the *Brachiaria-Urochoa* species complex. By 'associated with' in this context is meant that the bacteria or fungus lives on, in or in close proximity to the plant. For example, it may be endophytic, for example living within the internal tissues of the plant, or epiphytic, for example growing externally on the plant.

The plant material used to prepare the samples is from a plant of the *Brachiaria-Urochloa* species complex. More particularly, the plant of the *Brachiaria-Urochloa* species complex is selected from the group consisting of *Brachiaria brizantha, Brachiaria decumbens, Brachiaria humidicola, Brachiaria stolonifera, Brachiaria ruziziensis, Urochloa brizantha, Urochloa decumbens, Urochloa humidicola, Urochloa mosambicensis, Brachiaria marlothii, Brachiaria nigropedata, Urochloa dictyoneura, Urochloa oligotricha, Urochloa panicoides, Brachiaria obtusiflora, Brachiaria serrifolia, Urochloa advena, Urochloa arrecta, Urochloa brachyura, Urochloa Urochloa mollis, Urochloa xantholeuca, Urochloa oligotricha, Urochloa panicoides, Urochloa plantaginea, Urochloa platynota, Urochloa xantholeuca, Brachiaria holosericea, Brachiaria reptans, Brachiaria milliformis,* and *Brachiaria distachya,* as well as interspecific and intraspecific hybrids of *Brachiaria-Urochloa* species complex.

In a particularly preferred embodiment, the plant of the *Brachiaria-Urochloa* complex is selected from the group consisting of *Brachiaria brizantha, Brachiaria decumbens, Brachiaria humidicola, Brachiaria ruziziensis* and *Urochloa mosambicensis.*

Preferably, the samples of plant material are selected from the group consisting of leaf, stem, root and seed material. Even more preferably, samples of leaf, stem and root types are provided. Alternatively, samples of seed are provided. In another preferred embodiment samples of leaf, stem, root and seed material are provided.

By 'subjecting said samples to metagenomic analysis' as used herein is meant that metagenomic sequence data is generated from the plant material. More particularly, genetic material recovered from the plant samples is analysed to produce bacterial and/or fungal sequence data.

The term 'recovering genetic material' includes the extraction of genetic material, including DNA, from the sample of plant material.

The genetic material recovered from the plant samples may be enriched for DNA from endophytic strains (such as bacterial and/or fungal DNA) closely associated with the plant, as part of the process of recovering the genetic material from the sample of plant material.

Accordingly, in a preferred embodiment, the step of providing samples of plant material from plant species of the *Brachiaria-Urochloa* species complex includes the steps of:
grinding the plant material;
washing the ground plant material with alcohol; and
extracting nucleic acid from the alcohol wash.

In this aspect of the invention, preferably the plant material is plant seed. Preferably the plant material is roughly ground. Preferably the alcohol is ethanol, more preferably 100% ethanol. Preferably the ground plant material is washed multiple times, for example two times with alcohol. Preferably the nucleic acid is DNA.

Applicants have surprisingly found that it is possible to reduce the amount of plant nucleic acid, e.g. plant seed nucleic acid and/or enrich for nucleic acid from endophytic strains by roughly grinding the plant tissue, e.g. seed, and then washing this in alcohol, preferably ethanol. While applicants do not wish to be restricted by theory, it is thought that the alcohol acts to preserve the microbe component of the plant material, particularly seed. Extracting nucleic acid, e.g. DNA from the alcohol, e.g. ethanol, wash reduces the amount of host plant nucleic acid and enriches for microbe nucleic acid. This overcomes or at least alleviates the problem of one or more prior art methods, including those which generate large numbers of sequence reads to capture the microbial component or use differences in nucleic acid, e.g. DNA methlylation density to distinguish between host and microbial nucleic acid.

In a preferred embodiment, universal polymerase chain reaction (PCR) primers for profiling bacterial microbiome and/or fungal microbiome may be used to generate the sequence data. For example, primers directed to the 16S rDNA gene, more particularly the V4 region of the 16S rDNA gene, may be used for profiling bacterial microbiome. For example, primers directed to the internal transcribed spacer (ITS) region of rDNA genes, more particularly the ITS2 region of rDNA genes, may be used for profiling fungal microbiome.

In one embodiment, bacterial sequence data is produced using universal primers directed to the V4 region of the 16S rDNA gene and the fungal sequence data is produced using universal primers directed to the ITS2 region of the rDNA genes.

Metagenomic sequence data may be assembled to create the bacterial and/or fungal operational taxonomic units (OTUs). Preferably, the metagenomic sequence data may be quality trimmed and then paired using a paired-end assembler for sequences, such as PANDAseq, to create the bacterial and/or fungal OTUs.

The OTUs may be aligned against a bacterial database, such as the GreenGenes bacterial database, and/or a fungal database, such as the UNITE fungal database, to assign taxonomy.

The number of sequences associated with OTUs may be calculated for each sample.

By comparing the OTUs present in each sample species, core, supplemental and unique microbiomes may be identified. By a 'microbiome' is meant the collective genomes of the bacteria and/or fungi. By a 'core microbiome' is meant OTUs that are found across all or substantially all *Brachiaria-Urochloa* species tested. By a 'supplemental microbiome' is meant OTUs that are found across a subset of the *Brachiaria-Urochloa* species tested. By a 'unique microbiome' is meant OTUs associated with specific *Brachiaria-Urochloa* species.

Endophytes having a desired core, supplemental or unique microbiome may then be selected. For example, endophytes with a broad host range may be selected as candidates for delivery of traits into plants of the *Brachiaria-Urochloa* species complex. For example, endophytes with a narrow or specific host range may be selected as candidates for specific traits of interest, for example for production of compounds that provide beneficial properties such as improved tolerance to water and/or nutrient stress, or improved resistance to pests and/or diseases in the plant with which the endophyte is associated. In a preferred embodiment, the beneficial properties include insecticidal or insect repellent activity. In a further preferred embodiment, the improved resistance to pests and/or diseases includes antifungal activity. In a particularly preferred embodiment the compound may be an inhibitory compound, such as a nitrification inhibitor, for example a fusicoccane such as brachialactone.

In a second aspect of the present invention there is provided a substantially purified or isolated endophyte selected from the group consisting of *Hypocrea* sp./*Acre-* monium sp., *Acremonium* sp., *Microsphaeropsis arundis*, and *Sarocladium* sp./*Acremonium* sp., as described herein. Preferably said endophyte is isolated, selected and/or characterised by a method as hereinbefore described.

Representative samples, namely *Hypocrea* sp./*Acremonium* sp. 2.15.A.2, *Acremonium* sp. 2.3.C.1, *Microsphaeropsis arundis* 2.10.D 0.1, *Sarocladium* sp./*Acremonium* sp. 2.12.B.1, *Sarocladium* sp./*Acremonium* sp. 2.10.C.2 and *Sarocladium* sp. 2.11.B.1 were deposited, under the Budapest Treaty, at The National Measurement Institute, 1/153 Bertie Street, Port Melbourne, Victoria, Australia, 3207, on 22 Sep. 2015 with accession numbers V15/028236, V15/028237, V15/028238, V15/028239, V15/028240, V15/028241 and V15/028242, respectively.

By 'substantially purified' is meant that the endophyte is free of other organisms. The term therefore includes, for example, an endophyte in axenic culture. Preferably, the endophyte is at least approximately 90% pure, more preferably at least approximately 95% pure, even more preferably at least approximately 98% pure, even more preferably at least approximately 99% pure. Preferably the endophyte is in axenic culture.

The term 'isolated' means that the endophyte is removed from its natural environment (e.g. the natural environment if it is naturally occurring). For example, a naturally occurring endophyte present in a living plant is not isolated, but the same endophyte separated from some or all of the coexisting materials in the natural system, is isolated.

In its natural environment, the endophyte may live mutualistically within a plant. Alternatively, the endophyte may be an epiphyte, i.e. grow attached to or upon a plant. The endophyte may be a fungal endophyte or a bacterial endophyte.

The endophyte of the present invention may, in its natural environment, be associated with a plant of the *Brachiaria-Urochloa* species complex. More particularly, the plant of the *Brachiaria Urochloa* species complex is selected from the group consisting of *Brachiaria brizantha*, *Brachiaria decumbens*, *Brachiaria humidicola*, *Brachiaria stolonifera*, *Brachiria ruziziensis*, *Urochloa brizantha*, *Urochloa decumbens*, *Urochloa humidicola*, *Urochloa mosambicensis*, *Brachiaria marlothii*, *Brachiaria nigropedata*, *Urochloa dictyoneura*, *Urochloa oligotricha*, *Urochloa panicoides*, *Brachiaria obtusiflora*, *Brachiaria serrifolia*, *Urochloa advena*, *Urochloa arrecta*, *Urochloa brachyura*, *Urochloa eminii*, *Urochloa mollis*, *Urochloa xantholeuca*, *Urochloa oligotricha*, *Urochloa panicoides*, *Urochloa plantaginea*, *Urochloa platynota*, *Urochloa xantholeuca*, *Brachiaria holosericea*, *Brachiaria reptans*, *Brachiaria milliformis*, and *Brachiaria distachya*, as well as interspecific and intraspecific hybrids of *Brachiaria-Urochloa* species complex.

In a particularly preferred embodiment, the plant of the *Brachiaria-Urochloa* complex is selected from the group consisting of *Brachiaria brizantha*, *Brachiaria decumbens*, *Brachiaria humidicola*, *Brachiaria ruziziensis* and *Urochloa mosambicensis*.

By 'associated with' in this context is meant that the endophyte lives on, in or in close proximity to the plant. For example, it may be endophytic, for example living within the internal tissues of the plant, or epiphytic, for example growing externally on the plant.

The fungus may be a heterotroph that uses organic carbon for growth, more particularly a saprotroph that obtains nutrients by consuming detritus.

In a further aspect, the present invention provides a plant inoculated with an endophyte as hereinbefore described, said plant comprising an endophyte-free host plant stably infected with said endophyte. Preferably, said plant is a plant with which the endophyte is not naturally associated.

In a preferred embodiment, the plant with which the endophyte is associated has improved resistance to pests and/or diseases relative to an uninoculated control plant. Preferably, the improved resistance to pests and/or diseases includes insecticidal or insect repellent activity. In a further preferred embodiment, the improved resistance to pests and/or diseases includes antifungal activity.

In a preferred embodiment, the endophyte or plant with which the endophyte is associated may produce one or more compounds that provide beneficial properties such as improved tolerance to water and/or nutrient stress, or improved resistance to pests and/or diseases in the plant with which the fungus is associated. In a preferred embodiment, the beneficial properties include insecticidal or insect repellent activity. In a further preferred embodiment, the improved resistance to pests and/or diseases includes antifungal activity.

In a particularly preferred embodiment, the endophyte or plant with which the endophyte is associated may produce an inhibitory compound, such as a nitrification inhibitor, for example a fusicoccane such as brachialactone.

In a preferred embodiment, the host plant may be inoculated with more than one endophyte strain according to the present invention.

Preferably, the plant is an agricultural plant such as a grass species, preferably forage, turf or bioenergy grasses, or a grain crop or industrial crop grass.

The forage, turf or bioenergy grass may be those belonging to the *Brachiaria-Urochloa* species complex (panic grasses) including *Brachiaria brizantha*, *Brachiaria decumbens*, *Brachiaria humidicola*, *Brachiaria stolonifera*, *Brachiaria ruziziensis*, *B. dictyoneura*, *Urochloa brizantha*, *Urochloa decumbens*, *Urochloa humidicola*, *Urochloa mosambicensis* as well as interspecific and intraspecific hybrids of *Brachiaria-Urochloa* species complex, and those belonging to the genera *Lolium* and *Festuca*, including *L. perenne* (perennial ryegrass) and *L. arundinaceum* (tall fescue) and *L. multiflorum* (Italian ryegrass).

The grain crop or industrial crop grass may be those belonging to the genus *Triticum*, including *T. aestivum* (wheat), those belonging to the genus *Hordeum*, including *H. vulgare* (barley), those belonging to the genus *Zea*, including *Z. mays* (maize or corn), those belonging to the genus *Oryza*, including *O. sativa* (rice), those belonging to the genus *Saccharum* including *S. officinarum* (sugarcane), those belonging to the genus *Sorghum* including *S. bicolor* (sorghum), those belonging to the genus *Panicum*, including *P. virgatum* (switchgrass), and those belonging to the genera *Miscanthus*, *Paspalum*, *Pennisetum*, *Poa*, *Eragrostis* and *Agrostis*.

Preferably, the plant is infected with the endophyte by a method selected from the group consisting of inoculation breeding, crossing, hybridization, transduction, transfection, transformation and/or gene targeting; and combinations thereof.

The endophyte-infected plants may be cultured by known techniques. The person skilled in the art can readily determine appropriate culture conditions depending on the plant to be cultured.

In a further aspect, the present invention provides a plant, plant seed or other plant part derived from a plant of the present invention and stably infected with an endophyte of the present invention. Preferably, the plant, plant seed or other plant part with which the endophyte is associated has improved resistance to pests and/or diseases relative to an uninoculated control plant, plant seed or other plant part. In a preferred embodiment, the improved resistance to pests and/or diseases includes insecticidal or insect repellent activity. In a further preferred embodiment, the improved resistance to pests and/or diseases includes antifungal activity.

In a particularly preferred embodiment, endophyte or plant with which the endophyte is associated may produce an inhibitory compound, such as a nitrification inhibitor, for example a fusicoccane such as brachialactone.

Preferably, the plant cell, plant, plant seed or other plant part is from a grass, more preferably a forage, turf, bioenergy, grain crop or industrial crop grass.

The forage, turf or bioenergy grass may be those belonging to the *Brachiaria-Urochloa* species complex (panic grasses), including *Brachiaria brizantha, Brachiaria decumbens, Brachiaria humidicola, Brachiaria stolonifera, Brachiaria ruziziensis, B. dictyoneura, Urochloa brizantha, Urochloa decumbens, Urochloa humidicola, Urochloa mosambicensis* as well as interspecific and intraspecific hybrids of *Brachiaria-Urochloa* species complex such as interspecific hybrids between *Brachiaria ruziziensis x Brachiaria brizantha, Brachiaria ruziziensis x Brachiaria decumbens*, [*Brachiaria ruziziensis x Brachiaria decumbens*] x *Brachiaria brizantha*, [*Brachiaria ruziziensis x Brachiaria brizantha*] x *Brachiaria decumbens* and those belonging to the genera *Lolium* and *Festuca*, including *L. perenne* (perennial ryegrass) and *L. arundinaceum* (tall fescue) and *L. multiflorum* (Italian ryegrass).

The grain crop or industrial crop grass may be those belonging to the genus *Triticum*, including *T. aestivum* (wheat), those belonging to the genus *Hordeum*, including *H. vulgare* (barley), those belonging to the genus *Zea*, including *Z. mays* (maize or corn), those belonging to the genus *Oryza*, including *O. sativa* (rice), those belonging to the genus *Saccharum* including *S. officinarum* (sugarcane), those belonging to the genus *Sorghum* including *S. bicolor* (sorghum), those belonging to the genus *Panicum*, including *P. virgatum* (switchgrass), and those belonging to the genera *Miscanthus, Paspalum, Pennisetum, Poa, Eragrostis* and *Agrostis*.

By 'plant cell' is meant any self-propagating cell bounded by a semi-permeable membrane and containing plastid. Such a cell also required a cell wall if further propagation is desired. Plant cell, as used herein includes, without limitation, seeds suspension cultures, embryos, meristematic regions, callus tissue, leaves, roots, shoots, gametophytes, sporophytes, pollen and microspores.

In a further aspect, the present invention provides use of an endophyte as hereinbefore described to produce a plant stably infected with said endophyte. Preferably, the plant with which the endophyte is associated has improved resistance to pests and/or diseases relative to an uninoculated control plant. In a preferred embodiment, the improved resistance to pests and/or diseases includes insecticidal or insect repellent activity. In a further preferred embodiment, the improved resistance to pests and/or diseases includes antifungal activity.

In a preferred embodiment, the endophyte or plant with which the endophyte is associated may produce one or more compounds that provide beneficial properties such as improved tolerance to water and/or nutrient stress, or improved resistance to pests and/or diseases in the plant with which the fungus is associated. In a preferred embodiment, the beneficial properties include insecticidal or insect repellent activity. In a further preferred embodiment, the improved resistance to pests and/or diseases includes antifungal activity.

In a particularly preferred embodiment, the endophyte or plant with which the endophyte is associated may produce an inhibitory compound, such as a nitrification inhibitor, for example a fusicoccane, such as brachialactone.

In another preferred embodiment, the plant with which the endophyte is associated is a forage, turf, bioenergy, grain crop or industrial crop grass as hereinbefore described.

In a further aspect of the present invention, there is provided a method of increasing resistance to pests and/or diseases in a plant, said method including inoculating said plant with an endophyte as hereinbefore described. Preferably, the plant with which the endophyte is associated has improved resistance to pests and/or diseases relative to an uninoculated control plant. In a preferred embodiment, the improved resistance to pests and/or diseases includes insecticidal or insect repellent activity. In a further preferred embodiment, the improved resistance to pests and/or diseases includes antifungal activity.

In yet another preferred embodiment, the plant with which the endophyte is associated is a forage, turf, bioenergy, grain crop or industrial crop grass as hereinbefore described.

In another aspect, the present invention provides a method of producing a fusicoccane, said method including
   isolating an endophyte from a plant of the *Brachiaria-Urochoa* species complex;
   growing said endophyte in a suitable culture medium; and
   recovering one or more organic compounds including the fusicoccane from endophyte cells, from the culture medium, or from air space associated with the culture medium or endophyte.

Preferably the endophyte is an endophyte as hereinbefore described.

Preferably, the fusicoccane is compound of formula I:

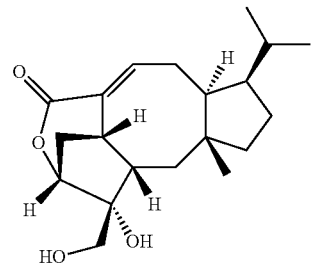

otherwise known as bracialactone, or a derivative, an isomer and/or a salt thereof.

Preferably, the plant of the *Brachiaria-Urochoa* species complex is selected from the group consisting of *Brachiaria brizantha, Brachiaria decumbens, Brachiaria humidicola, Brachiaria stolonifera, Brachiaria ruziziensis, Urochloa brizantha, Urochloa decumbens, Urochloa humidicola, Urochloa mosambicensis, Brachiaria marlothii, Brachiaria nigropedata, Urochloa dictyoneura, Urochloa oligotricha, Urochloa panicoides, Brachiaria obtusiflora, Brachiaria serrifolia, Urochloa advena, Urochloa arrecta, Urochloa brachyura, Urochloa Urochloa mollis, Urochloa xantholeuca, Urochloa oligotricha, Urochloa panicoides, Urochloa plantaginea, Urochloa platynota, Urochloa xantholeuca, Brachiaria holosericea, Brachiaria reptans,*

*Brachiaria milliformis,* and *Brachiaria distachya,* as well as interspecific and intraspecific hybrids of *Brachiaria-Urochloa* species complex.

Preferably the endophyte is grown in a culture medium including a source of carbohydrates. The source of carbohydrates may be a starch/sugar-based agar or broth such as potato dextrose agar, potato dextrose broth or half potato dextrose agar or a cereal-based agar or broth such as oatmeal agar or oatmeal broth. Other sources of carbohydrates can include endophyte agar, Murashige and Skoog with 20% sucrose, half V8 juice/half PDA, water agar and yeast malt extract agar.

In a preferred embodiment, the endophyte may be cultured in a culture medium including potato dextrose or oatmeal, for example potato dextrose agar, half potato dextrose agar, oatmeal agar, potato dextrose broth or oatmeal broth. Most preferably, the fungus may be cultured in a culture medium including oatmeal.

The endophyte may be cultured under aerobic or anaerobic conditions.

The endophyte may be cultured for a period of approximately 1 to approximately 100 days, more preferably from approximately 1 to approximately 50 days more preferably from approximately 1 to approximately 10 days.

In a preferred embodiment, the endophyte may be cultured in a bioreactor. By a 'bioreactor' is meant a device or system that supports a biologically active environment, such as a vessel in which is carried out a chemical process involving fungi of the present invention and/or products thereof. The chemical process may be aerobic or anaerobic. The bioreactor may have a volume ranging in size from milliliters to cubic metres, for example from approximately 50 millilitres to approximately 50,000 litres. The bioreactor may be operated via batch culture, batch feed culture, perfusion culture or continuous culture, for example continuous culture in a stirred-tank bioreactor. Endophytes cultured in the bioreactor may be suspended or immobilised.

The method includes the step of recovering one or more organic compounds including the fusicoccane from endophyte cells, from the culture medium, or from air space associated with the culture medium or endophyte.

For example, the organic compound(s) may be recovered from intracellular tissues, from the culture medium into which the endophyte may secrete liquids, or from the air space into which the endophyte may secrete vapours.

Vapours may arise directly from the endophyte or from the secreted liquids which transition between vapour and liquid phases.

The step of recovering the organic compound(s) is preferably done by separating cells from the culture medium or capturing vapours associated with the culture medium or endophyte.

Preferably the organic compound(s) is then isolated or purified by a method selected from the group consisting of gas chromatography, liquid chromatography, fractional distillation, cryogenic distillation, membrane separation and absorption chromatography, such as pressure, vacuum or temperature swing adsorption.

By an 'organic compound' is meant a chemical compound, the molecules of which contain the element carbon.

In a preferred embodiment, the organic compound may be a hydrocarbon such as a volatile hydrocarbon or a liquid hydrocarbon. Most preferably, the organic compound may be a volatile hydrocarbon.

By a 'hydrocarbon' is meant an organic compound comprising the elements carbon and hydrogen.

The term 'volatile' in this context is meant an organic compound which can evaporate or sublimate at standard laboratory temperature and pressure. Volatile organic compounds include those with a high vapour pressure, low boiling point and/or low molecular weight.

In a further aspect of the present invention there is provided a method of producing a fusicoccane in a plant of the *Brachiaria-Urochoa* species complex, said method including:

providing a plant of the *Brachiaria-Urochoa* species complex; and an endophyte, preferably an endophyte as hereinbefore described;

infecting said plant with said endophyte to form a symbiota;

growing the symbiota in a suitable culture medium, so that the fusicoccane is produced.

Preferably, the plant of the *Brachiaria-Urochoa* species complex is selected from the group consisting of *Brachiaria brizantha, Brachiaria decumbens, Brachiaria humidicola, Brachiaria stolonifera, Brachiaria ruziziensis, Urochloa brizantha, Urochloa decumbens, Urochloa humidicola, Urochloa mosambicensis, Brachiaria marlothii, Brachiaria nigropedata, Urochloa dictyoneura, Urochloa oligotricha, Urochloa panicoides, Brachiaria obtusiflora, Brachiaria serrifolia, Urochloa advena, Urochloa arrecta, Urochloa brachyura, Urochloa Urochloa mollis, Urochloa xantholeuca, Urochloa oligotricha, Urochloa panicoides, Urochloa plantaginea, Urochloa platynota, Urochloa xantholeuca, Brachiaria holosericea, Brachiaria reptans, Brachiaria milliformis,* and *Brachiaria distachya,* as well as interspecific and intraspecific hybrids of *Brachiaria-Urochloa* species complex.

Preferably, the plant is infected with the endophyte by a method selected from the group consisting of inoculation, breeding, crossing, hybridization, transduction, transfection, transformation and/or gene targeting; and combinations thereof.

The endophyte-infected plants may be cultured by known techniques. The person skilled in the art can readily determine appropriate culture conditions depending on the plant to be cultured.

In a further aspect, the present invention provides a plant, plant seed or other plant part derived from a plant produced by the method of the present invention and stably infected with an endophyte of the present invention. Preferably, the plant, plant seed or other plant part with which the endophyte is associated has improved resistance to pests and/or diseases relative to an uninoculated control plant, plant seed or other plant part. In a preferred embodiment, the improved resistance to pests and/or diseases includes insecticidal or insect repellent activity. In a further preferred embodiment, the improved resistance to pests and/or diseases includes antifungal activity.

In a particularly preferred embodiment, the endophyte or plant with which the endophyte is associated may produce an inhibitory compound, such as a nitrification inhibitor, for example a fusicoccane such as brachialactone.

Preferably, the plant cell, plant, plant seed or other plant part is from a grass, more preferably a forage, turf, bioenergy, grain crop or industrial crop grass.

The forage, turf or bioenergy grass may be those belonging to the *Brachiaria-Urochloa* species complex (panic grasses), including *Brachiaria brizantha, Brachiaria decumbens, Brachiaria humidicola, Brachiaria stolonifera, Brachiaria ruziziensis, B. dictyoneura, Urochloa brizantha, Urochloa decumbens, Urochloa humidicola, Urochloa*

*mosambicensis* as well as interspecific and intraspecific hybrids of *Brachiaria-Urochloa* species complex such as interspecific hybrids between *Brachiaria ruziziensis x Brachiaria brizantha*, *Brachiaria ruziziensis x Brachiaria decumbens*, [*Brachiaria ruziziensis x Brachiaria decumbens*] x *Brachiaria brizantha*, [*Brachiaria ruziziensis x Brachiaria brizantha*] x *Brachiaria decumbens* and those belonging to the genera *Lolium* and *Festuca*, including *L. perenne* (perennial ryegrass) and *L. arundinaceum* (tall fescue) and *L. multiflorum* (Italian ryegrass).

The grain crop or industrial crop grass may be those belonging to the genus *Triticum*, including *T. aestivum* (wheat), those belonging to the genus *Hordeum*, including *H. vulgare* (barley), those belonging to the genus *Zea*, including *Z. mays* (maize or corn), those belonging to the genus *Oryza*, including *O. sativa* (rice), those belonging to the genus *Saccharum* including *S. officinarum* (sugarcane), those belonging to the genus *Sorghum* including *S. bicolor* (sorghum), those belonging to the genus *Panicum*, including *P. virgatum* (switchgrass), and those belonging to the genera *Miscanthus, Paspalum, Pennisetum, Poa, Eragrostis* and *Agrostis*.

In another aspect, the present invention provides a method of inoculating a plant of the *Brachiaria-Urochoa* species complex with one or more endophytes, said method including providing sterilised seed of the plant of the *Brachiaria-Urochloa* species complex;

germinating the seed under aseptic conditions to produce host plants that are substantially free of microbial organisms;

inoculating the host plants with the one or more endophytes.

While Applicant does not wish to be restricted by theory, it is thought that conducting the method of the present invention under aseptic conditions ensures endophytes are inoculated into host plants that are substantially free of microbial organisms, thereby facilitating a high frequency of successful inoculation. Further, it is thought that the use of different media prior to inoculation to allow the host plant to establish, such as root growth promoting media, also facilitates high inoculation frequency. The use of a sterile environment also enables analysis of the microbiome without contamination.

For example the inoculation frequency may be between approximately 25% and approximately 100%, more preferably between approximately 50% and approximately 100%, even more preferably between approximately 75% and approximately 100%. The inoculation frequency may be higher than conventional methods.

Preferably, the plant of the *Brachiaria-Urochoa* species complex is of a species as hereinbefore described.

Preferably said one or more endophytes are selected from the endophytes as hereinbefore described. The one or more endophytes may be bacterial or fungal or a mixture thereof. In a preferred embodiment, the step of germinating the seed under aseptic conditions to produce host plants may include growing the germinated seed on shoot multiplication medium such as M3B and root multiplication medium such as MS+ NAA. Preferably, the germinated seed may be grown on shoot multiplication medium, splitting the resulting shoots into single tillers and then transferring them to root multiplication medium. The single tillers may be grown on the root multiplication medium for approximately 1 to approximately 6 weeks, more preferably approximately 2 to approximately 3 weeks, to promote root growth. The resulting plantlets may again be split into single tillers for endophyte inoculation.

In a preferred embodiment, the step of inoculating the host plants with the one or more endophytes may include removal of the outer sheath to reveal shoot initial, creation of a wound in the shoot meristem and inoculation into the wound.

In a preferred embodiment, the method may include the further step of retaining the plantlets on sterile media following inoculation, preferably for a period of approximately 1 to approximately 6 weeks, more preferably approximately 2 to approximately 3 weeks.

In a preferred embodiment, the method may include the still further step of transferring the inoculated plants thus produced to soil or similar medium for further growth, for example under glasshouse conditions.

The present invention will now be more fully described with reference to the accompanying Examples and drawings. It should be understood, however, that the description following is illustrative only and should not be taken in any way as a restriction on the generality of the invention described above.

BRIEF DESCRIPTION OF THE DRAWINGS/FIGURES

FIG. 1 shows the incidence of endophyte isolates in *brachiaria* species based on rDNA sequence analysis of the internal transcribed spacer (ITS) and 18S coding regions. *Brachiaria* endophyte isolates are genetically diverse, representing at least 10 distinct taxonomic groups.

FIG. 2 shows a bootstrap consensus tree generated through neighbour-joining analysis of the ITS region from fungal endophyte isolates derived from *Brachiaria-Urochloa* accessions (left hand side) and the identification of the presence/absence of selected isolated and culturable fungal endophyte strains in the microbiomes of 5 *Brachiaria-Urochloa* species (right hand side) (Bb—*B. brizantha*; Bh—*B. humidicola*; Bd—*B. decumbens*; Um—*U. mosambicensis*; Br—*B. ruziensis*) based on the ITS sequence.

Figure 6:
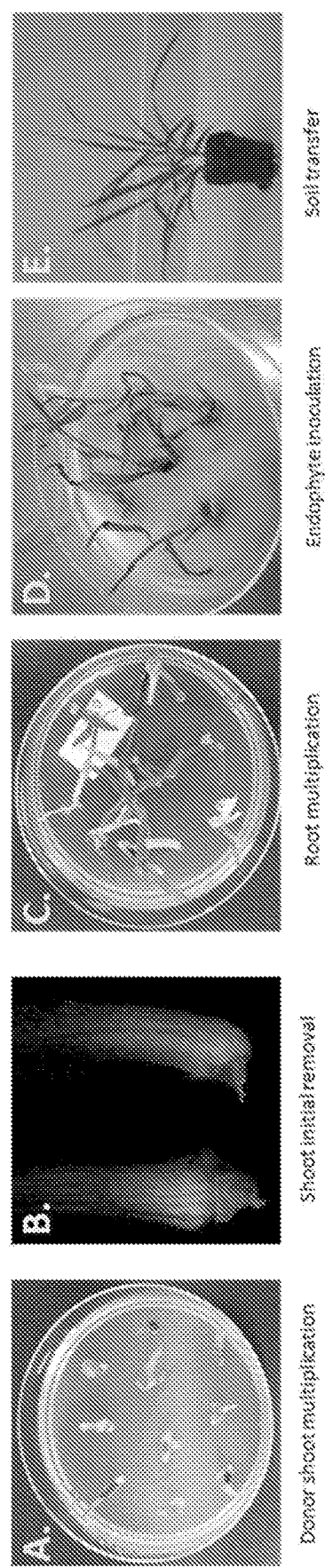

FIG. 6 shows consecutive stages of an optimised endophyte inoculation procedure for *Brachiaria-Urochola*. A. Microbe-free donor plantlets grown on shoot multiplication media (M3B) under sterile conditions; B. Donor shoots split into single tillers and transferred to root multiplication media (MS+NAA); C. Single tillers grown for 2-3 weeks to promote root growth prior to splitting plantlets into single tillers, removal of the outer sheath to reveal shoot initial, transferral to water agar and inoculation into a small cut is made across the shoot meristem; D. Inoculated plantlets retained on ½ MS media for 2 weeks; E. Plantlets after transfer to soil and growth under glasshouse conditions for 8 weeks.

Figure 7:
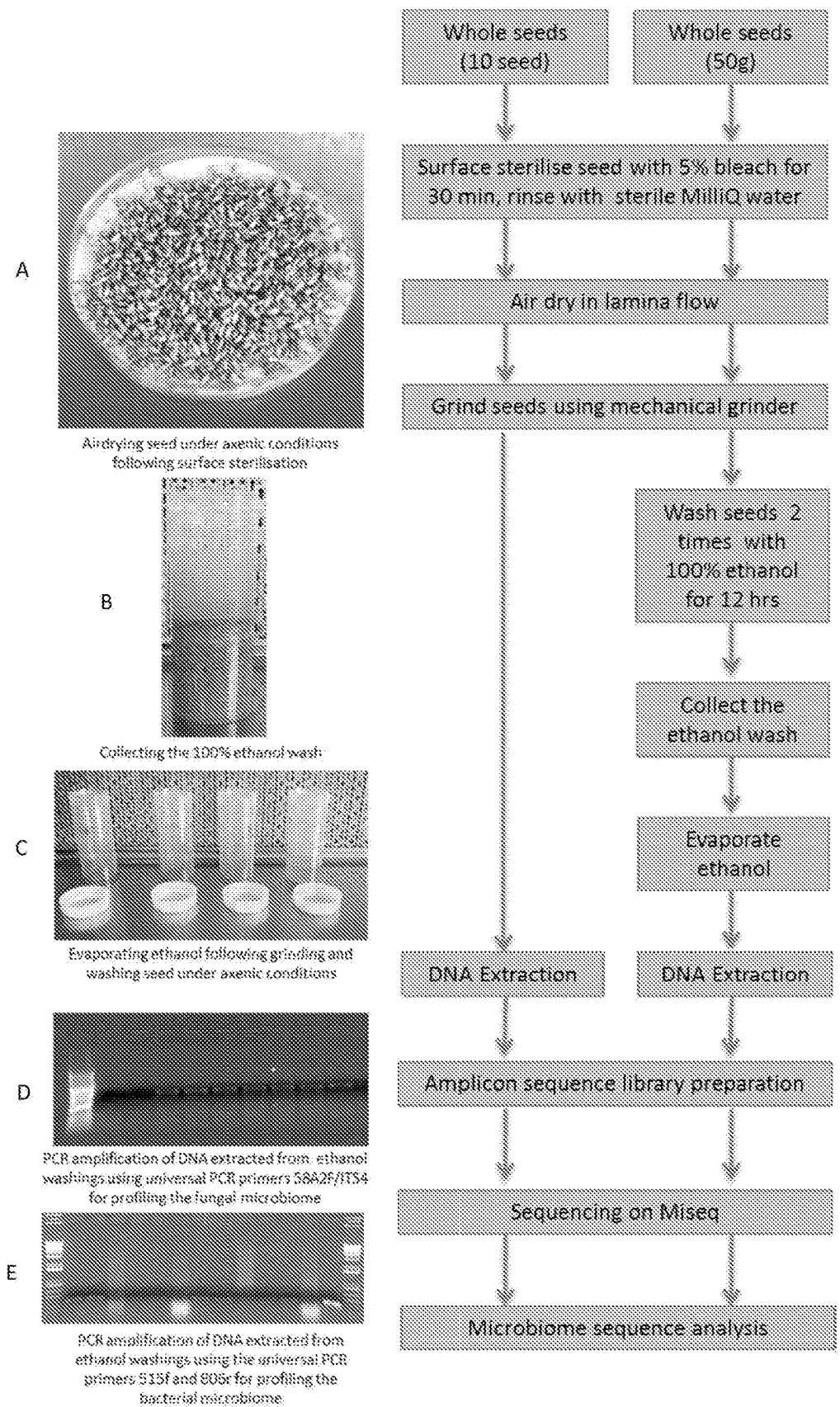

FIG. 7 shows a flow chart describing a method for profiling the seed associated bacterial and fungal microbiome. The accompanying photographs show each stage of the method of enriching for bacterial and fungal DNA from 50 g seed from one accession. A. Air drying the seeds prior to grinding; B. Collecting the 100% ethanol wash. The supernatant contains the seed associated endophytic microbiome; C. Vials during evaporation of ethanol; D. Analysis of extracted DNA from each of the 10 Accessions (columns 1 to 10) to determine presence of fungal DNA. E. Analysis of extracted DNA to determine presence of bacterial DNA.

DETAILED DESCRIPTION OF THE EMBODIMENTS

Example 1—Endophytic Microbial Profile of Brachiaria-Urochloa Species

The endophytic microbiomes of five *Brachiaria-Urochloa* species were profiled using metagenomics. Species included *B. brizantha*, *B. humidicola*, *B. ruziziensis*, *B. decumbens* and *U. mosambicensis*. A total of three plants were profiled per species. Three organs were profiled from each plant (roots, stem and leaves). A total of two replicates were prepared per organ, per plant. Plant material (approximately 100 mg) was surface sterilised by soaking in 70% ethanol for 30 seconds, followed by 4.2% NaOCl (bleach) for 2 minutes, and then rinsed three to five times in sterile MilliQ water to ensure the sterilant had been completely removed. Samples were freeze-dried for 48 hours at −58° C. and 0.014 mBar. DNA was extracted using the Qiagen DNeasy plant mini kit according to manufacturer's instructions. Endophytic bacteria and fungi were evaluated in the metagenomics analyses using the universal PCR primers 515f and 806r for profiling the bacterial microbiome (V4 region of the 16S rDNA gene, approx. 350 base pairs), and 58A2F and ITS4 for the fungal microbiome (ITS2 region of the rDNA genes, approx. 400 base pairs), with associated Illumina adapters. Paired end libraries were prepared and loaded according to the corresponding Illumina user guide. Metagenomic sequence data was quality trimmed and paired using PANDSEQ to create operational taxonomic units (OTU), which were aligned against the GreenGenes bacterial database and the UNITE fungal database to assign taxonomy (OTU: 97% sequence identity, e-value <10e-110). The number of sequences associated with OTUs was calculated across all samples, and normalised as a percentage.

Total Microbial Diversity Across *Brachiaria-Urochloa*

A total of 361 bacterial operational taxonomic units (OTUs) were identified across all *Brachiaria-Urochloa* species, comprising 25 bacterial Phyla, 56 Classes, 121 Families and 170 Genera (including candidate taxonomic groups) (Table 1). The analyses identified the core microbiome (OTUs found across all *Brachiaria-Urochloa* species) and the unique microbiome (OTUs associated with specific *Brachiaria-Urochloa* species), along with bacterial OTUs only associated with *Brachiaria-Urochloa* species known to produce brachialactone (*B. humidicola* and *B. ruziziensis*) (Table 1). The analyses also provided cross validation of the presence of endophytes isolated from these *Brachiaria-Urochloa* species.

In addition, 84 fungal OTUs were identified, comprising 5 Phyla, 14 Classes, 32 Families and 44 Genera (Table 2). The analyses identified the core microbiome (OTUs found across all *Brachiaria-Urochloa* species) and the unique microbiome (OTUs associated with specific *Brachiaria-Urochloa* species), along with fungal OTUs only associated with *Brachiaria-Urochloa* species known to produce brachialactone (*B. humidicola* and *B. ruziziensis*) (Table 2). The analyses also provide cross validation of the presence of endophytes isolated from these *Brachiaria-Urochloa* species.

TABLE 1

Endophytic bacterial OTUs found within the leaves, root and stem of five *Brachiaria-Urochloa* species (361 OTUs), including identification of the core microbiome, the unique microbiome, and bacterial OTUs only associated with *Brachiaria-Urochloa* species known to produce brachialactone (Brach - *B. humidicola* and *B. ruziziensis*). Examples of the bacterial microbial diversity in *Brachiaria-Urochloa* species is represented within *B. humidicola* (Bh) and *B. decumbens* (Bd).

| | Endophytic bacterial OTU | Leaves | Stems | Roots | Core | Unique | Isolated | Brach | Bh | Bd |
|---|---|---|---|---|---|---|---|---|---|---|
| 1 | Bacteria sp 1 | Y | Y | Y | Y | | | | Y | Y |
| 2 | Enterobacteriaceae sp | Y | Y | Y | Y | | | | Y | Y |
| 3 | Rhodospirillaceae sp | | Y | Y | Y | | | | Y | Y |
| 4 | Comamonadaceae sp | | Y | Y | Y | | | | Y | Y |
| 5 | *Agrobacterium* sp | | Y | Y | Y | | | | Y | Y |
| 6 | Alicyclobacillaceae sp | | | Y | Y | | | | Y | Y |
| 7 | Sphingobacteriaceae sp | | Y | Y | Y | | | | Y | Y |
| 8 | *Mycobacterium* sp | | | Y | Y | | | | Y | Y |
| 9 | *Bacillus* sp | | | Y | Y | | | | Y | Y |
| 10 | Chitinophagaceae sp | | Y | Y | Y | | | | Y | Y |
| 11 | *Pseudomonas* sp | Y | | Y | Y | | | | Y | Y |
| 12 | Caulobacteraceae sp | | Y | Y | Y | | | | Y | Y |
| 13 | *Rhodoplanes* sp | Y | | Y | Y | | | | Y | Y |
| 14 | *Rhizobium* sp | | Y | Y | Y | | | | Y | Y |
| 15 | Rhizobiales sp | | | Y | Y | | | | Y | Y |
| 16 | *Janthinobacterium* sp | | | Y | Y | | | | Y | Y |
| 17 | *Cellulomonas* sp | | | Y | Y | | | | Y | Y |
| 18 | *Herbaspirillum* sp | | Y | Y | Y | | | | Y | Y |
| 19 | *Flavobacterium* sp | | | Y | Y | | | | Y | Y |
| 20 | Xanthomonadaceae sp | | | Y | Y | | | | Y | Y |
| 21 | Solirubrobacterales sp | | | Y | Y | | | | Y | Y |
| 22 | *Dyella* sp *ginsengisoli* | | | Y | Y | | | | Y | Y |
| 23 | Betaproteobacteria sp 1 | | | Y | Y | | | | Y | Y |
| 24 | *Opitutus* sp | Y | | Y | Y | | | | Y | Y |
| 25 | *Aquicella* sp | | | Y | Y | | | | Y | Y |
| 26 | Candidatus_Xiphinematobacter sp | | | Y | Y | | | | Y | Y |

TABLE 1-continued

Endophytic bacterial OTUs found within the leaves, root and stem of five Brachiaria-Urochloa species (361 OTUs), including identification of the core microbiome, the unique microbiome, and bacterial OTUs only associated with Brachiaria-Urochloa species known to produce brachialactone (Brach - B. humidicola and B. ruziziensis). Examples of the bacterial microbial diversity in Brachiaria-Urochloa species is represented within B. humidicola (Bh) and B. decumbens (Bd).

| | Endophytic bacterial OTU | Leaves | Stems | Roots | Core | Unique | Isolated | Brach | Bh | Bd |
|---|---|---|---|---|---|---|---|---|---|---|
| 27 | Microbacterium sp | | | Y | Y | | | | Y | Y |
| 28 | Flavobacterium sp succinicans | | Y | Y | Y | | | | Y | Y |
| 29 | Kiloniellales sp | | Y | Y | Y | | | | Y | Y |
| 30 | Alphaproteobacteria sp 1 | Y | | Y | Y | | | | Y | Y |
| 31 | Devosia sp | | | Y | Y | | | | Y | Y |
| 32 | Planctomyces sp | Y | | Y | Y | | | | Y | Y |
| 33 | Sphingomonadaceae sp | Y | | Y | Y | | | | Y | Y |
| 34 | Isosphaeraceae sp | | | Y | Y | | | | Y | Y |
| 35 | Asticcacaulis sp biprosthecium | | | Y | Y | | | | Y | Y |
| 36 | Pirellulaceae sp 1 | Y | | Y | Y | | | | Y | Y |
| 37 | Myxococcales sp 1 | Y | | Y | Y | | | | Y | Y |
| 38 | Gammaproteobacteria sp | | | Y | Y | | | | Y | Y |
| 39 | Mycobacterium sp vaccae | | | Y | Y | | | | Y | Y |
| 40 | Chitinophaga sp | | Y | Y | Y | | | | Y | Y |
| 41 | Dechloromonas sp | Y | | Y | Y | | | | Y | Y |
| 42 | Streptomyces sp | | | Y | Y | | | | Y | Y |
| 43 | Desulfosporosinus sp meridiei | | | Y | Y | | | | Y | Y |
| 44 | Rhodocyclaceae sp | | | Y | Y | | | | Y | Y |
| 45 | Novosphingobium sp | | | Y | Y | | | | Y | Y |
| 46 | Oxalobacteraceae sp | | | Y | Y | | | | Y | Y |
| 47 | Opitutaceae sp | | | Y | Y | | | | Y | Y |
| 48 | Hyphomicrobium sp | | | Y | Y | | | | Y | Y |
| 49 | Legionellaceae sp | | | Y | Y | | | | Y | Y |
| 50 | Rhodanobacter sp | | | Y | Y | | | | Y | Y |
| 51 | Sinobacteraceae sp | Y | | Y | Y | | | | Y | Y |
| 52 | Sphingobium sp | | | Y | Y | | | | Y | Y |
| 53 | Nocardioidaceae sp | | | Y | Y | | | | Y | Y |
| 54 | Azospirillum sp | | Y | Y | Y | | | | Y | Y |
| 55 | Acidobacteria sp 1 | | | Y | Y | | | | Y | Y |
| 56 | Alphaproteobacteria sp 2 | | | Y | Y | | | | Y | Y |
| 57 | Klebsiella sp | | | Y | Y | | | | Y | Y |
| 58 | Pleomorphomonas sp oryzae | | | Y | Y | | | | Y | Y |
| 59 | Rhizobiaceae sp | | | Y | Y | | | | Y | Y |
| 60 | Bacillus sp ginsengihumi | | | Y | Y | | | | Y | Y |
| 61 | Rhodobacteraceae sp | | | Y | Y | | | | Y | Y |
| 62 | Cytophagaceae sp | Y | | Y | Y | | | | Y | Y |
| 63 | Bradyrhizobium sp | | | Y | Y | | | | Y | Y |
| 64 | Methylotenera sp mobilis | | | Y | Y | | | | Y | Y |
| 65 | Microbacterium sp chocolatum | | | Y | | | | | Y | Y |
| 66 | Acidobacteria sp 2 | | | Y | Y | | | | Y | Y |
| 67 | Rhodobacter sp | | | Y | | | | | | Y |
| 68 | Coxiellaceae sp | | | Y | Y | | | | Y | Y |
| 69 | Acidimicrobiales sp 1 | | | Y | Y | | | | Y | Y |
| 70 | Mesorhizobium sp | | | Y | Y | | | | Y | Y |
| 71 | Cellvibrio sp | | | Y | Y | | | | Y | Y |
| 72 | Methylibium sp | | | Y | Y | | | | Y | Y |
| 73 | Rubrivivax sp gelatinosus | | | Y | Y | | | | Y | Y |
| 74 | Clostridium sp | | | Y | Y | | | | Y | Y |
| 75 | Erythrobacteraceae sp | | | Y | Y | | | | Y | Y |
| 76 | Pedosphaerales sp 1 | Y | | Y | Y | | | | Y | Y |
| 77 | Microbacteriaceae sp | | | Y | Y | | | | Y | Y |
| 78 | Thermomicrobia sp | | | Y | Y | | | | Y | Y |
| 79 | Hyphomicrobiaceae sp | | | Y | Y | | | | Y | Y |
| 80 | Bacteria sp 2 | | | Y | Y | | | | Y | Y |
| 81 | Sphingobacteriales sp | | | Y | Y | | | | Y | Y |
| 82 | Bradyrhizobiaceae sp | | | Y | Y | | | | Y | Y |
| 83 | Acetobacteraceae sp | | Y | Y | Y | | | | Y | Y |
| 84 | Phaeospirillum sp fulvum | | | Y | | | | | | Y |
| 85 | Legionella sp | | | Y | Y | | | | Y | Y |
| 86 | Dyella sp | | | Y | Y | | | | Y | Y |
| 87 | Gemmata sp | | | Y | Y | | | | Y | Y |

TABLE 1-continued

Endophytic bacterial OTUs found within the leaves, root and stem of five *Brachiaria-Urochloa* species (361 OTUs), including identification of the core microbiome, the unique microbiome, and bacterial OTUs only associated with *Brachiaria-Urochloa* species known to produce brachialactone (Brach - *B. humidicola* and *B. ruziziensis*). Examples of the bacterial microbial diversity in *Brachiaria-Urochloa* species is represented within *B. humidicola* (Bh) and *B. decumbens* (Bd).

| | Endophytic bacterial OTU | Leaves | Stems | Roots | Core | Unique | Isolated | Brach | Bh | Bd |
|---|---|---|---|---|---|---|---|---|---|---|
| 88 | *Hydrogenophaga* sp | | | Y | Y | | | | Y | Y |
| 89 | Betaproteobacteria sp 2 | | Y | Y | Y | | | | Y | Y |
| 90 | *Rhodanobacter* sp *lindaniclasticus* | | | Y | Y | | | | Y | Y |
| 91 | *Pedobacter* sp | | | Y | Y | | | | Y | Y |
| 92 | *Asticcacaulis* sp | | | Y | Y | | | | Y | Y |
| 93 | *Magnetospirillum* sp | | | Y | Y | | | | Y | Y |
| 94 | *Prosthecobacter* sp | | Y | Y | Y | | | | Y | Y |
| 95 | *Paenibacillus* sp | | | Y | Y | | | | Y | Y |
| 96 | *Sphingomonas* sp *wittichii* | | | Y | Y | | | | Y | Y |
| 97 | Methylophilaceae sp | | | Y | Y | | | | Y | Y |
| 98 | *Sphingomonas* sp | | | Y | Y | | | | Y | Y |
| 99 | *Chryseobacterium* sp | | | Y | | | | | | Y |
| 100 | Chloroflexi sp 1 | | | Y | | | | | Y | Y |
| 101 | *Propionivibrio* sp | | | Y | Y | | | | Y | Y |
| 102 | *Phenylobacterium* sp | | | Y | Y | | | | Y | Y |
| 103 | *Delftia* sp | | | Y | Y | | | | Y | Y |
| 104 | Bacillales sp | | | Y | Y | | | | Y | Y |
| 105 | *Erwinia* sp | | | Y | Y | | | | Y | Y |
| 106 | *Limnohabitans* sp | | | Y | Y | | | | Y | Y |
| 107 | *Cohnella* sp | | | Y | Y | | | | Y | Y |
| 108 | *Denitrobacter* sp | | | Y | Y | | | | Y | Y |
| 109 | *Kaistia* sp | | | Y | Y | | | | Y | |
| 110 | *Dyadobacter* sp | | | Y | | | | | | Y |
| 111 | Alphaproteobacteria sp 3 | | | Y | | | | | | Y |
| 112 | *Sphingomonas* sp *azotifigens* | | | Y | | | | | Y | Y |
| 113 | Actinomycetales sp | | | Y | Y | | | | Y | Y |
| 114 | Pirellulaceae sp 2 | | | Y | Y | | | | Y | Y |
| 115 | *Fluviicola* sp | | | Y | Y | | | | Y | Y |
| 116 | *Shinella* sp | | | Y | Y | | | | Y | Y |
| 117 | *Spirochaeta* sp *aurantia* | | | Y | | | | | Y | Y |
| 118 | Brucellaceae sp | | | Y | | | | | | Y |
| 119 | *Agrobacterium* sp *sullae* | | | Y | Y | | | | Y | Y |
| 120 | Fibrobacteria sp | Y | | Y | Y | | | | Y | Y |
| 121 | Alteromonadales sp 1 | | | Y | Y | | | | Y | Y |
| 122 | Nakamurellaceae sp | | | Y | Y | | | | Y | Y |
| 123 | Alcaligenaceae sp | | | Y | Y | | | | Y | Y |
| 124 | *Desulfovibrio* sp | | | Y | Y | | | | Y | Y |
| 125 | *Sediminibacterium* sp | | | Y | Y | | | | Y | Y |
| 126 | *Cryocola* sp | | | Y | | | | | | Y |
| 127 | *Sphingopyxis* sp | | | Y | | | | | | Y |
| 128 | *Burkholderia* sp | | | Y | Y | | | | Y | Y |
| 129 | Gaiellaceae sp | | | Y | | | | | Y | Y |
| 130 | *Niastella* sp | | | Y | | | | | Y | Y |
| 131 | *Rathayibacter* sp | | | Y | | | | | | Y |
| 132 | *Pandoraea* sp | | | Y | | | | | Y | Y |
| 133 | Burkholderiales sp | | | Y | Y | | | | Y | Y |
| 134 | *Thermomonas* sp | | | Y | | | | | | Y |
| 135 | *Novosphingobium* sp *capsulatum* | | | Y | Y | | | | Y | Y |
| 136 | *Pseudomonas* sp *nitroreducens* | | | Y | Y | | | | Y | Y |
| 137 | Lachnospiraceae sp | | | Y | | | | | | Y |
| 138 | Bacteria sp 3 | | | Y | Y | | | | Y | Y |
| 139 | Caldilineaceae sp | | | Y | | | | | | Y |
| 140 | Micrococcaceae sp | | | Y | | | | | | Y |
| 141 | Bacteria sp 4 | | | Y | | | | | Y | Y |
| 142 | *Geobacillus* sp | | | Y | | | | | Y | Y |
| 143 | *Salinibacterium* sp | | | Y | | | | | | Y |
| 144 | Rickettsiales sp | | | Y | Y | | | | Y | Y |
| 145 | Cyanobacteria sp 1 | | | Y | Y | | | | Y | Y |
| 146 | Hyphomonadaceae sp | Y | | Y | | | | | Y | Y |
| 147 | *Salinispora* sp *tropica* | | | Y | | | | | Y | Y |
| 148 | *Bdellovibrio* sp | | | Y | | | | | | Y |
| 149 | *Caulobacter* sp | | | Y | Y | | | | Y | Y |
| 150 | *Salinispora* sp | | | Y | Y | | | | Y | Y |
| 151 | *Sulfurospirillum* sp | | | Y | | | | | | Y |

TABLE 1-continued

Endophytic bacterial OTUs found within the leaves, root and stem of five *Brachiaria-Urochloa* species (361 OTUs), including identification of the core microbiome, the unique microbiome, and bacterial OTUs only associated with *Brachiaria-Urochloa* species known to produce brachialactone (Brach - *B. humidicola* and *B. ruziziensis*). Examples of the bacterial microbial diversity in *Brachiaria-Urochloa* species is represented within *B. humidicola* (Bh) and *B. decumbens* (Bd).

| | Endophytic bacterial OTU | Leaves | Stems | Roots | Core | Unique | Isolated | Brach | Bh | Bd |
|---|---|---|---|---|---|---|---|---|---|---|
| 152 | *Uliginosibacterium* sp | | | Y | Y | | | | Y | Y |
| 153 | *Bdellovibrio* sp *bacteriovorus* | | | Y | | | | | Y | Y |
| 154 | Chloroflexi sp 2 | | | Y | | | | | | Y |
| 155 | Ruminococcaceae sp | | | Y | | | | | | Y |
| 156 | Anaerolineae sp 1 | Y | | Y | | | | | Y | Y |
| 157 | *Kyrpidia* sp | | | Y | Y | | | | Y | Y |
| 158 | *Rhodoferax* sp | | | Y | | | | | Y | |
| 159 | Aurantimonadaceae sp | | | Y | | | | | | Y |
| 160 | *Curtobacterium* sp | | | Y | | | | | Y | Y |
| 161 | *Cupriavidus* sp | | | Y | Y | | | | Y | Y |
| 162 | *Nocardioides* sp | | | Y | | | | | Y | Y |
| 163 | Legionellales sp | | | Y | | | | | | Y |
| 164 | *Coprococcus* sp | | | Y | Y | | | | Y | Y |
| 165 | Pseudomonadaceae sp | | | Y | | | | | | |
| 166 | *Emticicia* sp | | | Y | Y | | | | Y | Y |
| 167 | Procabacteriaceae sp | | | Y | | | | | | Y |
| 168 | Aeromonadaceae sp | | | Y | | | | | | Y |
| 169 | *Cytophaga* sp | | | Y | | | | | | Y |
| 170 | Haliangiaceae sp | | | Y | | | | | | Y |
| 171 | Chloroflexi sp 3 | | | Y | | | | | Y | Y |
| 172 | Gemmatimonadetes sp 1 | | | Y | | | | | Y | Y |
| 173 | Betaproteobacteria sp 3 | | | Y | | | | | Y | Y |
| 174 | *Demequina* sp | | | Y | | | | | | Y |
| 175 | Cyanobacteria sp 2 | | | Y | | | | | | Y |
| 176 | Moraxellaceae sp | | | Y | | | | | | |
| 177 | Chlorobi sp 1 | | | Y | | | | | Y | Y |
| 178 | Bacteriovoracaceae sp | | | Y | | | | | | Y |
| 179 | *Paludibacter* sp | | | Y | | | | | Y | Y |
| 180 | *Burkholderia* sp *bryophila* | | | Y | | | | | Y | Y |
| 181 | Porphyromonadaceae sp | | | Y | | | | | Y | Y |
| 182 | *Leptothrix* sp | | | Y | | | | | Y | Y |
| 183 | Gemmataceae sp | | | Y | | | | | | Y |
| 184 | *Aminobacter* sp | | | Y | | | | | Y | Y |
| 185 | *Desulfovibrio* sp *mexicanus* | | | Y | | | | | | Y |
| 186 | *Flavihumibacter* sp | | | Y | | | | | | Y |
| 187 | *Ramlibacter* sp | | | Y | | | | | | Y |
| 188 | Neisseriaceae sp | | | Y | | | | | | Y |
| 189 | *Asteroleplasma* sp | | | Y | | | | | Y | Y |
| 190 | *Edaphobacter* sp *modestum* | | | Y | | | | | | Y |
| 191 | Verrucomicrobiaceae sp | | | Y | | | | | Y | Y |
| 192 | Patulibacteraceae sp | | | Y | | | | | Y | Y |
| 193 | *Arthrospira* sp | | | Y | | | | | | Y |
| 194 | *Achromobacter* sp | | | Y | | | | | | Y |
| 195 | *Desulfobulbus* sp | | | Y | | | | | | Y |
| 196 | *Pelomonas* sp | | | Y | | | | | | Y |
| 197 | *Zoogloea* sp | | | Y | | | | | | Y |
| 198 | *Desulfovibrio* sp *putealis* | | | Y | Y | | | | Y | Y |
| 199 | *Salmonella* sp *enterica* | | | Y | | | | | | Y |
| 200 | Acidimicrobiales sp 2 | | | Y | | | | | Y | Y |
| 201 | Bacteria sp 5 | | | Y | | | | | | Y |
| 202 | Phyllobacteriaceae sp | | | Y | | | | | | Y |
| 203 | *Dokdonella* sp | | | Y | | | | | | Y |
| 204 | Pedosphaerales sp 2 | | | Y | | | | | | Y |
| 205 | *Variovorax* sp *paradoxus* | | | Y | | | | | Y | Y |
| 206 | Armatimonadetes sp | | | Y | | | | | | Y |
| 207 | Bacteroidales sp | | | Y | | | | | Y | |
| 208 | Chloroflexi sp 4 | | | Y | | | | | | Y |
| 209 | *Geobacter* sp | | | Y | | | Y | | Y | |
| 210 | Deltaproteobacteria sp 1 | | | Y | | | | | | Y |
| 211 | *Sulfuricurvum* sp *kujiense* | | | Y | | | | | | Y |
| 212 | *Phaeospirillum* sp | | | Y | | | | | Y | |
| 213 | *Tatlockia* sp | | | Y | | | | | | Y |
| 214 | *Terriglobus* sp | | | Y | | | | | Y | Y |
| 215 | *Pelosinus* sp | | | Y | | | | | | Y |

TABLE 1-continued

Endophytic bacterial OTUs found within the leaves, root and stem of five *Brachiaria-Urochloa* species (361 OTUs), including identification of the core microbiome, the unique microbiome, and bacterial OTUs only associated with *Brachiaria-Urochloa* species known to produce brachialactone (Brach - *B. humidicola* and *B. ruziziensis*). Examples of the bacterial microbial diversity in *Brachiaria-Urochloa* species is represented within *B. humidicola* (Bh) and *B. decumbens* (Bd).

| | Endophytic bacterial OTU | Leaves | Stems | Roots | Core | Unique | Isolated | Brach | Bh | Bd |
|---|---|---|---|---|---|---|---|---|---|---|
| 216 | *Thermomonas* sp *fusca* | | Y | Y | | | | Y | Y | |
| 217 | *Gemmata* sp *obscuriglobus* | | | Y | | | | | | |
| 218 | *Telmatospirillum* sp | | | Y | | | | | | Y |
| 219 | *Luteibacter* sp *rhizovicinus* | | | Y | | | | | Y | Y |
| 220 | *Acidisoma* sp | | | Y | | | | | Y | Y |
| 221 | *Fimbriimonas* sp | | | Y | | | | | | Y |
| 222 | *Janibacter* sp | | | Y | | | | | | Y |
| 223 | Anaerolineae sp 2 | | | Y | | | | | | Y |
| 224 | Chloroflexi sp 5 | | | Y | | | | | | Y |
| 225 | *Thermoanaerobacterium* sp *saccharolyticum* | | | Y | | | | Y | Y | |
| 226 | *Luteolibacter* sp | | | Y | | | | | | |
| 227 | *Leadbetterella* sp | | | Y | | | | | | Y |
| 228 | *Afifella* sp | | | Y | | | | | Y | Y |
| 229 | Microthrixaceae sp | | | Y | | | | | | Y |
| 230 | Chlorobi sp 2 | | | Y | | | | | Y | |
| 231 | *Ancylobacter* sp | | | Y | | | | | | |
| 232 | *Steroidobacter* sp | Y | | Y | | | | | Y | Y |
| 233 | *Singulisphaera* sp | | | Y | | | | | | Y |
| 234 | *Luteimonas* sp | | | Y | | | | | | Y |
| 235 | Gemmatimonadetes sp 2 | | | Y | | | | Y | Y | |
| 236 | *Bosea* sp genosp. | | | Y | | | | | | Y |
| 237 | *Salinibacterium* sp *amurskyense* | | | Y | | | | | | Y |
| 238 | Pedosphaerales sp 3 | | | Y | | | | | | Y |
| 239 | *Phycicoccus* sp | | | Y | | | | | | Y |
| 240 | *Spirosoma* sp | | | Y | | | | | | Y |
| 241 | Chromatiales sp | | | Y | | Bd | | | | Y |
| 242 | *Rathayibacter* sp *caricis* | | | Y | | | | | | Y |
| 243 | *Treponema* sp | | | Y | | | | | Y | Y |
| 244 | Holophagaceae sp | | | Y | | | | | | Y |
| 245 | *Anaerovorax* sp | | | Y | | | | | | Y |
| 246 | Desulfobulbaceae sp | | | Y | | | | | Y | |
| 247 | *Reichenbachiella* sp | | | Y | | | | | | |
| 248 | *Nannocystis* sp | | | Y | | Ur | | Y | | |
| 249 | Polyangiaceae sp | | | Y | | | | | | Y |
| 250 | *Haererehalobacter* sp *salaria* | | | Y | | | | | | Y |
| 251 | *Streptomyces* sp *lanatus* | | | Y | | | | | | Y |
| 252 | *Aquitalea* sp *magnusonii* | | | Y | | | | | | Y |
| 253 | *Erwinia* sp *soli* | | | Y | | | | Y | | |
| 254 | *Trabulsiella* sp | | | Y | | | | | | Y |
| 255 | *Pilimelia* sp | | | Y | | | | | Y | Y |
| 256 | Clostridia sp | | | Y | | | | | Y | Y |
| 257 | *Ammoniphilus* sp | | | Y | | | | Y | | |
| 258 | Paenibacillaceae sp | | | Y | | | | | | Y |
| 259 | Streptosporangiaceae sp | | | Y | | | | | | |
| 260 | Methylocystaceae sp | | | Y | | | | Y | | |
| 261 | Solibacterales sp | | | Y | | | | | | Y |
| 262 | Acidobacteria sp 3 | | | Y | | | | | | Y |
| 263 | Frankiaceae sp | | | Y | | | | | | Y |
| 264 | *Acidovorax* sp *delafieldii* | | | Y | | | | | | |
| 265 | Piscirickettsiaceae sp | | | Y | | | | | | Y |
| 266 | Candidatus_Solibacter sp | | | Y | | Bd | | | | Y |
| 267 | *Parvibaculum* sp | | | Y | | | | Y | Y | |
| 268 | Betaproteobacteria sp 4 | | | Y | | | | Y | Y | |
| 269 | Acidobacteria sp 4 | | | Y | | Bb | | | | |
| 270 | *Cellulomonas* sp *uda* | | | Y | | | | Y | | |
| 271 | Chloroflexi sp 6 | Y | | Y | | | | | Y | Y |
| 272 | *Brevibacillus* sp *reuszeri* | | | Y | | | | Y | Y | |
| 273 | *Blastomonas* sp | | | Y | | | | | | Y |
| 274 | Bacteria sp 6 | | | Y | | | | | | Y |
| 275 | Streptomycetaceae sp | | | Y | | | | | | Y |

TABLE 1-continued

Endophytic bacterial OTUs found within the leaves, root and stem of five *Brachiaria-Urochloa* species (361 OTUs), including identification of the core microbiome, the unique microbiome, and bacterial OTUs only associated with *Brachiaria-Urochloa* species known to produce brachialactone (Brach - *B. humidicola* and *B. ruziziensis*). Examples of the bacterial microbial diversity in *Brachiaria-Urochloa* species is represented within *B. humidicola* (Bh) and *B. decumbens* (Bd).

| | Endophytic bacterial OTU | Leaves | Stems | Roots | Core | Unique | Isolated | Brach | Bh | Bd |
|---|---|---|---|---|---|---|---|---|---|---|
| 276 | *Sphingomonas* sp *echinoides* | | | Y | | | | | | Y |
| 277 | *Polaromonas* sp | | | Y | | | | | | Y |
| 278 | Cellulomonadaceae sp | | | Y | | Bd | | | | Y |
| 279 | *Armatimonadia* sp | | | Y | | Ur | Y | | | |
| 280 | Cyanobacteria sp 3 | | | Y | | Bb | | | | |
| 281 | *Comamonas* sp | | | Y | | Ur | Y | | | |
| 282 | Gracilibacteraceae sp | | | Y | | Ur | Y | | | |
| 283 | Cenarchaeaceae sp | | | Y | | | | | Y | |
| 284 | *Acidovorax* sp | | | Y | | | | | | |
| 285 | *Janthinobacterium* sp *lividum* | | | Y | | Ur | Y | | | |
| 286 | *Acinetobacter* sp | | | Y | | | | Y | | |
| 287 | *Ruminococcus* sp | | | Y | | Bd | | | | Y |
| 288 | *Simplicispira* sp | | | Y | | Ur | Y | | | |
| 289 | *Rheinheimera* sp | | | Y | | Um | | | | |
| 290 | *Pseudomonas* sp *stutzeri* | | | Y | | | | | | |
| 291 | Acidobacteriaceae sp | | | Y | | | | Y | Y | |
| 292 | Kouleothrixaceae sp | | | Y | | | | | | Y |
| 293 | *Azospira* sp | | | Y | | Ur | Y | | | |
| 294 | Chromatiaceae sp | | | Y | | | | | | Y |
| 295 | *Pseudomonas* sp *viridiflava* | | | Y | | Ur | Y | | | |
| 296 | *Staphylococcus* sp *aureus* | | | Y | | | | | | Y |
| 297 | Alteromonadaceae sp | | | Y | | | | | | Y |
| 298 | *Aeromicrobium* sp | | | Y | | Bb | | | | |
| 299 | *Chthoniobacter* sp | | | Y | | Ur | Y | | | |
| 300 | Saprospiraceae sp | | | Y | | Bb | | | | |
| 301 | *Bacillus* sp *coagulans* | | | Y | | Bd | | | | Y |
| 302 | *Frankia* sp | | | Y | | Bb | | | | |
| 303 | Kineosporiaceae sp | | | Y | | Bd | | | | Y |
| 304 | *Alicyclobacillus* sp | | | Y | | Ur | Y | | | |
| 305 | Sporolactobacillaceae sp | | | Y | | Ur | Y | | | |
| 306 | Pedosphaerales sp 4 | | | Y | | Bd | | | | Y |
| 307 | *Nocardia* sp | | | Y | | Bd | | | | Y |
| 308 | Planctomycetes sp | | | Y | | Bh | | Y | Y | |
| 309 | Syntrophobacteraceae sp | | | Y | | Bb | | | | |
| 310 | Bacteria sp 7 | | | Y | | Bd | | | | Y |
| 311 | Xanthobacteraceae sp | | | Y | | Bb | | | | |
| 312 | Saprospirales sp | | | Y | | Ur | Y | | | |
| 313 | *Geobacillus* sp *thermodenitrificans* | | | Y | | Ur | Y | | | |
| 314 | *Paenibacillus* sp *chondroitinus* | | | Y | | Ur | Y | | | |
| 315 | *Mycoplana* sp | | | Y | | Bd | | | | Y |
| 316 | *Corynebacterium* sp | | | Y | | Bb | | | | |
| 317 | *Microbacterium* sp *aurum* | | | Y | | Bd | | | | Y |
| 318 | Nostocaceae sp | | | Y | | Bb | | | | |
| 319 | *Thermoanaerobacterium* sp | | | Y | | Ur | Y | | | |
| 320 | Peptococcaceae sp | | | Y | | Bb | | | | |
| 321 | Clostridiales sp | | | Y | | Ur | Y | | | |
| 322 | *Ochrobactrum* sp | | | Y | | Bd | | | | Y |
| 323 | Myxococcales sp 2 | | | Y | | Bb | | | | |
| 324 | *Pseudomonas* sp *alcaligenes* | | | Y | | Ur | Y | | | |
| 325 | *Methanobacterium* sp | | | Y | | Bh | | Y | Y | |
| 326 | Methylophilales sp | | | Y | | Um | | | | |
| 327 | *Enterobacter* sp | | | Y | | Bd | | | | Y |
| 328 | *Niabella* sp | | | Y | | Ur | Y | | | |
| 329 | Bacillaceae sp | | | Y | | Um | | | | |
| 330 | *Balneimonas* sp | | | Y | | Bb | | | | |
| 331 | *Schlegelella* sp | | | Y | | Ur | Y | | | |
| 332 | Deltaproteobacteria sp 2 | | | Y | | Bb | | | | |
| 333 | Bacteria sp 8 | | | Y | | Ur | Y | | | |
| 334 | Chthoniobacteraceae sp | | | Y | | Bd | | | | Y |
| 335 | Acidobacteria sp 5 | | | Y | | Bd | | | | Y |
| 336 | *Inquilinus* sp | | | Y | | Bb | | | | |
| 337 | Myxococcaceae sp | | | Y | | Bd | | | | Y |

TABLE 1-continued

Endophytic bacterial OTUs found within the leaves, root and stem of five *Brachiaria-Urochloa* species (361 OTUs), including identification of the core microbiome, the unique microbiome, and bacterial OTUs only associated with *Brachiaria-Urochloa* species known to produce brachialactone (Brach - *B. humidicola* and *B. ruziziensis*). Examples of the bacterial microbial diversity in *Brachiaria-Urochloa* species is represented within *B. humidicola* (Bh) and *B. decumbens* (Bd).

| | Endophytic bacterial OTU | Leaves | Stems | Roots | Core | Unique | Isolated | Brach | Bh | Bd |
|---|---|---|---|---|---|---|---|---|---|---|
| 338 | *Prosthecobacter* sp *debontii* | | Y | | | Bd | | | | Y |
| 339 | *Dermacoccus* sp | | | Y | | Bd | | | | Y |
| 340 | Jonesiaceae sp | | | Y | | Ur | Y | | | |
| 341 | *Actinoplanes* sp | | | Y | | Bd | | | | Y |
| 342 | *Clostridium* sp *bowmanii* | | | Y | | Um | | | | |
| 343 | Bacteria sp 9 | | | Y | | Bd | | | | Y |
| 344 | *Chromobacterium* sp | | | Y | | Ur | Y | | | |
| 345 | *Tolumonas* sp | | | Y | | Um | | | | |
| 346 | Alteromonadales sp 2 | | | Y | | Bd | | | | Y |
| 347 | Bacteria sp 10 | | | Y | | Ur | Y | | | |
| 348 | *Corynebacterium* sp *kroppenstedtii* | Y | | | | Bh | | Y | Y | |
| 349 | *Cloacibacterium* sp | | | Y | | Bd | | | | Y |
| 350 | *Thermogemmatispora* sp | | | Y | | Bh | Y | Y | | |
| 351 | *Staphylococcus* sp *epidermidis* | | | Y | | Bd | | | | Y |
| 352 | *Sporomusa* sp | | | Y | | Bb | | | | |
| 353 | *Azovibrio* sp | | | Y | | Bb | | | | |
| 354 | Alteromonadales sp 3 | | | Y | | Ur | Y | | | |
| 355 | *Erwinia* sp *dispersa* | | | Y | | Ur | Y | | | |
| 356 | *Acinetobacter* sp *johnsonii* | | | Y | | Ur | Y | | | |
| 357 | *Bacteroides* sp | | | Y | | Bb | | | | |
| 358 | *Anaerococcus* sp | | | Y | | Bb | | | | |
| 359 | *Peptoniphilus* sp | | | Y | | Bb | | | | |
| 360 | *Acidocella* sp | | | Y | | Bh | Y | Y | | |
| 361 | Desulfovibrionaceae sp | | | Y | | Ur | Y | 0 | | |

TABLE 2

Endophytic fungal OTUs found within the leaves, root and stem of five *Brachiaria-Urochloa* species (84 OTUs), including identification of the core microbiome, the unique microbiome, and fungal OTUs only associated with *Brachiaria-Urochloa* species known to produce brachialactone (Brach - *B. humidicola* and *B. ruziziensis*). Examples of the fungal microbial diversity in *Brachiaria* species is represented within *B. humidicola* (Bh) and *B. decumbens* (Bd).

| | Endophytic fungal OTU | Leaves | Stems | Roots | Core | Unique | Isolated | Brach | Bh | Bd |
|---|---|---|---|---|---|---|---|---|---|---|
| 1 | Dothideomycetes sp | Y | Y | Y | Y | | | | Y | Y |
| 2 | Uncultured Fungal sp 1 (*Microdochium bolleyi*) | Y | Y | Y | Y | | Y | | Y | Y |
| 3 | *Fusarium proliferatum* | Y | Y | Y | Y | | | | Y | Y |
| 4 | *Lecythophora* sp | | | Y | Y | | | | Y | Y |
| 5 | Chaetosphaeriales sp | Y | Y | Y | Y | | | | Y | Y |
| 6 | *Sarocladium strictum* | | Y | Y | Y | | Y | | Y | Y |
| 7 | *Chaetomium* sp 1 | | | Y | Y | | | | Y | Y |
| 8 | Uncultured *Glomus* sp | | | Y | Y | | | | Y | Y |
| 9 | Sordariomycetes sp | | | Y | Y | | | | Y | Y |
| 10 | Uncultured Fungal sp (soil) | | | Y | Y | | | | Y | Y |
| 11 | *Hypocrea* sp | | | Y | Y | | Y | | Y | Y |
| 12 | *Coniochaeta* sp | | | Y | Y | | | | Y | Y |
| 13 | *Microsphaeropsis arundinis* | | | Y | Y | | Y | | Y | Y |
| 14 | Uncultured *Sebacina* sp 1 | | | Y | Y | | | | Y | Y |
| 15 | *Chrysosporium* sp 1 | | | Y | | | | | Y | Y |
| 16 | *Acremonium* sp | | Y | Y | | | Y | | | |
| 17 | *Podospora* sp 1 | | | Y | | | | | Y | Y |
| 18 | *Fusarium* sp | | | Y | | | | | Y | Y |
| 19 | *Fusarium oxysporum* f sp *ciceris* | | | Y | | | | | Y | Y |
| 20 | Uncultured Ascomycota sp | | | Y | | | | | Y | |
| 21 | *Rhizophagus* sp | | | Y | | | | | Y | Y |

TABLE 2-continued

Endophytic fungal OTUs found within the leaves, root and stem of five
Brachiaria-Urochloa species (84 OTUs), including identification of
the core microbiome, the unique microbiome, and fungal OTUs only
associated with Brachiaria-Urochloa species known to produce
brachialactone (Brach - B. humidicola and B. ruziziensis). Examples
of the fungal microbial diversity in Brachiaria species is
represented within B. humidicola (Bh) and B. decumbens (Bd).

| Endophytic fungal OTU | Leaves | Stems | Roots | Core | Unique | Isolated | Brach | Bh | Bd |
|---|---|---|---|---|---|---|---|---|---|
| 22 Cryptococcus laurentii | | | Y | | | | | | Y |
| 23 Flagelloscypha minutissima | | | Y | | | | | Y | |
| 24 Podospora communis | | | Y | | | | | Y | |
| 25 Cladosporium cladosporioides | | | Y | | | | | Y | Y |
| 26 Uncultured Rhizophagus sp | | | Y | | | | | Y | Y |
| 27 Exophiala cancerae | | | Y | | | | | Y | |
| 28 Uncultured Coprinus sp | | | Y | | | | | | Y |
| 29 Uncultured Olpidium sp | | | Y | | | | | Y | Y |
| 30 Rhizophagus irregularis | | | Y | | | | | Y | Y |
| 31 Uncultured Fungal sp 2 | | | Y | | | | | | |
| 32 Myrmecridium schulzeri | | | Y | | | | | Y | Y |
| 33 Uncultured Urediniomycete sp | | | Y | | | | | | |
| 34 Rhizophagus irregularis DAOM 181602 | | | Y | | | | | Y | Y |
| 35 Paraglomus brasilianum | | | Y | | | | | Y | Y |
| 36 Fungal sp 1 | | | Y | | | | | | |
| 37 Parascedosporium putredinis | | | Y | | | | | Y | Y |
| 38 Uncultured Sebacina sp 2 | | | Y | | | | | Y | Y |
| 39 Uncultured Acaulospora sp | | | Y | | | | Y | Y | |
| 40 Chaetomium thermophilum | | | Y | | | | | | Y |
| 41 Candida tropicalis | | | Y | | | | Y | | |
| 42 Conlarium sp | | | Y | | | | Y | | |
| 43 Arthrobotrys sp | | | Y | | | | | | Y |
| 44 Candida sp | | | Y | | | | Y | | |
| 45 Trichoderma harzianum | | | Y | | | | Y | Y | |
| 46 Pseudeurotium sp | | | Y | | Ur | | Y | | |
| 47 Chaetomium sp 2 | | | Y | | | | | | |
| 48 Doratomyces sp | | | Y | | | | | | Y |
| 49 Zopfiella marina | | | Y | | Um | | | | |
| 50 Monographella cucumerina | | | Y | | Bb | | Y | | |
| 51 Clitopilus scyphoides | | | Y | | | | | | Y |
| 52 Acephala sp | | | Y | | | | | Y | |
| 53 Trichurus sp | | | Y | | | | | Y | Y |
| 54 Corynascus sp | | | Y | | Ur | | Y | | |
| 55 Uncultured Archaeospora sp | | | Y | | Ur | | Y | | |
| 56 Trichoderma asperellum | | | Y | | Bb | | Y | | |
| 57 Gibberella fujikuroi | | | Y | | Um | | | | |
| 58 Fusarium sp | | | Y | | Ur | | Y | | |
| 59 Fungal sp 2 | | | Y | | Bh | | Y | Y | |
| 60 Fusarium oxysporum | | | Y | | Bh | | Y | Y | |
| 61 Peziza ostracoderma | | | Y | | Bb | | Y | | |
| 62 Pseudallescheria boydii | | | Y | | Um | | | | |
| 63 Fungal sp 3 | | | Y | | Um | | | | |
| 64 Pseudogymnoascus sp | | | Y | | Bh | Y | Y | Y | |
| 65 Claroideoglomus sp | | | Y | | Bh | | Y | Y | |
| 66 Leptosphaeria sp | | | Y | | Bh | | Y | Y | |
| 67 Uncultured Herpotrichiellaceae | | | Y | | Bh | | Y | Y | |
| 68 Haptocillium sinense | | | Y | | Bd | | | | Y |
| 69 Piriformospora indica | | | Y | | Um | | | | |
| 70 Fungal sp 4 | | | Y | | Um | | | | |
| 71 Exophiala sp | | | Y | | Bh | | Y | Y | |
| 72 Neotyphodium sp FaTG 2 | | | Y | | Bd | | | | Y |
| 73 Uncultured Trichoderma sp | | | Y | | Bb | | Y | | |
| 74 Podospora sp 2 | Y | | Y | | Bh | | Y | Y | |
| 75 Meira sp | | | Y | | Bh | | Y | Y | |
| 76 Leptosphaerulina chartarum | | | Y | | Ur | | Y | | |
| 77 Chrysosporium sp 2 | | | Y | | Bb | | Y | | |
| 78 Ilyonectria sp | | | Y | | Bh | | Y | Y | |

TABLE 2-continued

Endophytic fungal OTUs found within the leaves, root and stem of five Brachiaria-Urochloa species (84 OTUs), including identification of the core microbiome, the unique microbiome, and fungal OTUs only associated with Brachiaria-Urochloa species known to produce brachialactone (Brach - B. humidicola and B. ruziiensis). Examples of the fungal microbial diversity in Brachiaria species is represented within B. humidicola (Bh) and B. decumbens (Bd).

| Endophytic fungal OTU | Leaves | Stems | Roots | Core | Unique | Isolated | Brach | Bh | Bd |
|---|---|---|---|---|---|---|---|---|---|
| 79 Gibberella intricans | | | Y | | Um | | | | |
| 80 Ophiostoma stenoceras | | | Y | | Bh | | Y | Y | |
| 81 Microbotryomycetes sp | | | Y | | Um | | | | |
| 82 Cryptococcus podzolicus | | | Y | | Bb | | Y | | |
| 83 Fungal sp (endophyte) | | | Y | | Bb | | Y | | |
| 84 Fungal sp 5 | | | Y | | Bh | | Y | Y | |

Microbial Diversity Between Plant Organs of Brachiaria-Urochloa

Microbial diversity was greatest in the roots of Brachiaria-Urochloa species accounting for 359 bacterial species (99.4%) and 83 fungal species (98.8%) (Tables 1 and 2). The microbial diversity in the stem and leaf was significantly lower than the roots, accounting for 5-20 bacterial or fungal OTUs.

Microbial Diversity Across Brachiaria-Urochloa Species

The core microbiome consisted of 130 bacterial OTUs and 14 fungal OTUs (Tables 1, 2, and 3). The core bacterial microbiome contained a diverse array of taxa, while the core fungal microbiome predominantly contained Sordariomycetes species (8). The OTUs associated with the core microbiome were also the most abundant OTUs across all Brachiaria-Urochloa species. The number of OTUs unique to Brachiaria-Urochloa species ranged from 5 to 27 for bacteria and 2 to 12 for fungi, and were predominantly found in low abundance in their respective species.

humidicola had the second lowest bacterial diversity, approximately 31% lower than B. decumbens (highest bacterial diversity). As with all other Brachiaria-Urochloa species the greatest microbial diversity was observed in the roots, while there was very low microbial diversity in the stems and leaves. The number of bacterial and fungal OTUs associated with B. decumbens was 276 and 37 respectively. B. decumbens had the highest bacterial diversity, approximately 3 to 33% higher than any other Brachiaria-Urochloa species. Conversely, B. decumbens had the second lowest fungal diversity, approximately 23% lower than B. humidicola. As with all other Brachiaria-Urochloa species the greatest microbial diversity was observed in the roots, while there was very low microbial diversity in the stems and leaves.

The top five fungal and bacterial OTUs associated with both B. humidicola and B. decumbens show sequence homology to isolates from NCBI that have been predomi-

TABLE 3

The core and unique microbiome associated with Brachiaria-Urochloa species

| | | B. brizantha | B. decumbens | B. humidicola | U. mosambicensis | B. ruziiensis |
|---|---|---|---|---|---|---|
| Core | Bacteria | | | 130 | | |
| | Fungi | | | 14 | | |
| Unique | Bacteria | 19 | 23 | 5 | 5 | 27 |
| | Fungi | 7 | 2 | 12 | 8 | 5 |

Microbial Species Associated with B. Humidicola and B. decumbens

The number of bacterial and fungal OTUs associated with B. humidicola was 189 and 48 respectively. B. humidicola had the highest fungal diversity, approximately 15% higher than any other Brachiaria-Urochloa species. Conversely, B.

nantly been identified as endophytes, including endophytes of other Poaceae species (e.g. Oryzae sativa, Triticum aestivum), mycorrhizae (e.g. Glomus species) or rhizobacteria (Rhizobiales species). The fungal pathogen Fusarium proliferatum was also present, which is a seed-borne pathogen of a range of agricultural crop species (Tables 4 and 5).

TABLE 4

Examples of the most abundant fungal OTUs associated with Brachiaria-Urochloa species, and their corresponding NCBI top Blastn hit (accession number, e-value, isolation source, and endophytic origin - E+/−).

| | OTU (Unite Hit) | NCBI Hit | E+/− | Isolation Source | Accession | E-Value |
|---|---|---|---|---|---|---|
| 1 | Dothidiomycetes sp. | Fungal sp. | + | Trillium tschonoskii | GU479902.1 | 7.0E−149 |
| | | Fungal endophyte | + | Holcus lanatus | FN394695.1 | 7.0E−149 |

TABLE 4-continued

Examples of the most abundant fungal OTUs associated with
Brachiaria-Urochloa species, and their corresponding NCBI
top Blastn hit (accession number, e-value, isolation
source, and endophytic origin - E+/-).

| | OTU (Unite Hit) | NCBI Hit | E+/- | Isolation Source | Accession | E-Value |
|---|---|---|---|---|---|---|
| 2 | Uncultured Fungal sp | Microdochium bolleyi | + | Triticum aestivum | KC989068.1 | 3.0E-163 |
| | | Uncultured root-associated fungus | + | Sporobolus cryptandrus | FJ362153.1 | 1.0E-141 |
| 3 | Chaetosphaeriales sp. | Chaetosphaeriales sp. | + | Populus trichocarpa | KF428394.1 | 2.0E-149 |
| | | Chaetosphaeriaceae | + | Populus deltoides | JX244066.1 | 2.0E-149 |
| 4 | Fusarium proliferatum | Fusarium proliferatum | + | Dendrobium sp. | KM023784.1 | 2.0E-159 |
| | | Fusarium sp. | + | Saccharum officinarum | KF293339.1 | 2.0E-159 |
| 5 | Uncultured Glomus sp. | Uncultured Glomus | + | Allium cepa L. | AM992800.1 | 0.0E+00 |
| | | Uncultured Glomeromycota | + | Sequoiadendron giganteum | HQ895815.2 | 8.0E-179 |

TABLE 5

Examples of the most abundant bacterial OTUs associated with Brachiaria
species, and their corresponding NCBI top Blastn hit (accession number,
e-value, isolation source, and endophytic origin - E+/-).

| | OTU (GreenGenes Hit) | NCBI Hit | E+/- | Isolation Source | Accession | E-Value |
|---|---|---|---|---|---|---|
| 1 | Enterobacteriaceae sp | Enterobacter oryziphilus | - | Oryza sativa | NR_125587.1 | 2.0E-132 |
| | | Kosakonia sacchari | + | Saccharum officinarum | NR_118333.1 | 4.0E-129 |
| 2 | Pseudomonas sp | Pseudomonas fulva | - | Oryza sativa soil | NR_074659.1 | 2.0E-132 |
| | | Pseudomonas protegens Pf-5 | - | — | NR_074599.1 | 8.0E-131 |
| | | Pseudomonas entomophila | - | Soil | NR_102854.1 | 2.0E-127 |
| 3 | Agrobacterium sp | Agrobacterium tumefaciens | - | — | NR_041396.1 | 2.0E-132 |
| | | Rhizobium vignae | + | Astragalus dahuricus | NR_117440.1 | 4.0E-129 |
| | | Rhizobium paknamense | + | Lemna aequinoctialis | NR_114340.1 | 8.0E-126 |
| 4 | Comamonadaceae sp | Ottowia shaoguanensis | - | Coking wastewater | NR_125656.1 | 8.0E-131 |
| | | Comamonas granuli | - | — | NR_114013.1 | 4.0E-129 |
| | | Comamonas testosteroni | - | Activated sludge | NR_102841.1 | 2.0E-127 |
| 5 | Herbaspirillum sp | Herbaspirillum frisingense | + | Miscanthus sacchariflorus | NR_025353.1 | 2.00E-132 |
| | | Herbaspirillum huttiense | - | — | NR_024698.1 | 2.00E-132 |
| | | Oxalicibacterium horti | - | Soil | NR_112833.1 | 8.00E-126 |

Microbial Diversity Associated with Brachialactone Producing Brachiaria-Urochloa Species A total of 45 bacterial and 29 fungal OTUs were identified only in the Brachiaria-Urochloa species found to produce brachialactone, B. humidicola and/or B. ruziziensis (Tables 1 and 2). The OTUs associated with brachialactone producing Brachiaria-Urochloa species represent a range of diverse bacterial and fungal taxa.

Figure 1:
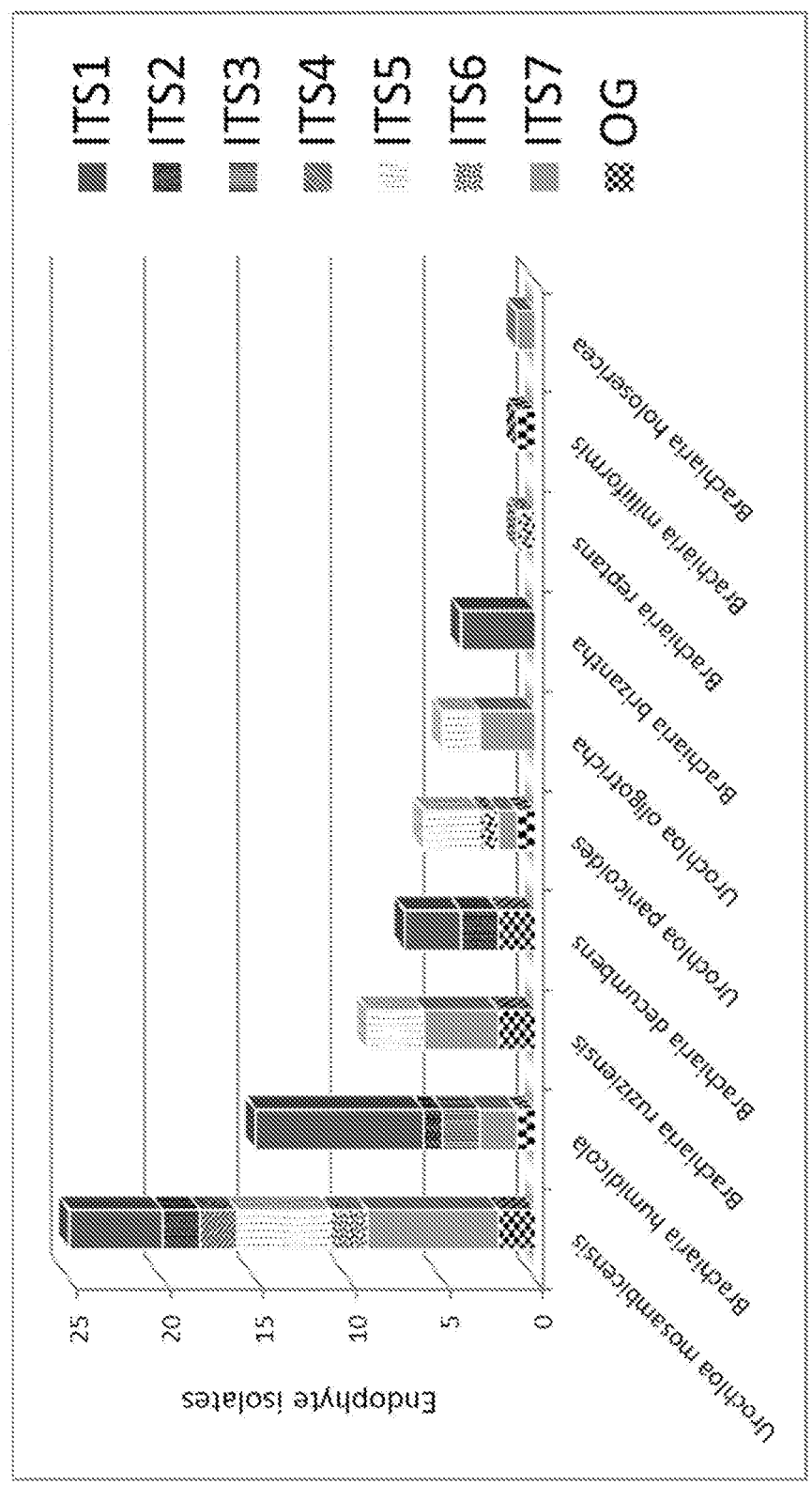

Example 2—Metagenome Analysis of the Brachiaria Microbiome Determines the Host Range of Fungal Endophytes of Brachiaria-Urochloa Grasses A total of 97 fungal endophyte isolates derived from 11 Brachiaria-Urochloa species were identified in a global study of 281 accessions from 23 countries. The internal transcribed spacer ITS sequence was used for further characterisation. The entire region of nuclear ribosomal DNA which comprises both internal transcribed spacers ITS1 and ITS2 and the 5.8δ subunit was PCR-amplified using primers ITS5 and ITS4 (White et al. 1990). Purified PCR amplification products were sequenced using Sanger sequencing technology. Isolated subcultured endophytes were then grouped based on ITS sequence identity. Ribosomal DNA (rDNA) sequence analysis based on the internal transcribed spacer (ITS) and 18S coding regions shows that brachiaria endophyte isolates are genetically diverse, representing at least 10 distinct taxonomic groups (FIG. 1). B. humidicola and *B. ruziensis* species, shown to produce brachialactone, exhibit high levels of fungal endophyte diversity and richness (FIG. 1).

Sequence data was used in BLASTN analysis to identify matches in the NCBI database. *Brachiaria* endophytes discovered are genetically novel. Comparison of each isolates ITS sequence to those in publically available databases did not identify any fungal strains with >90% identity. Phylogenetic analysis confirmed that isolates from different ITS clusters belonged to diverse genera. In several accessions, multiple endophytes isolated from a single plant belonged to different rDNA specific clusters, suggesting co-existence of multiple fungal endophyte species in the same plant (Table 6).

TABLE 6

Summary of fungal endophytes isolated from 11 *Brachiaria-Urochola* species.

| Host species | Host plant identification | No. of endophyte isolates |
| --- | --- | --- |
| B. decumbens | 1.1 | 1 |
| U. mosambicensis | 2.1 | 23 |
| B. holosericea | 2.3 | 1 |
| B. reptans | 2.4 | 1 |
| B. reptans | 2.4 | 3 |
| B. miliiformis | 2.5 | 1 |
| B. ruziensis | 2.6 | 2 |
| B. ruziensis | 2.7 | 7 |
| U. panicoides | 2.8 | 3 |
| U. mosambicensis | 2.9 | 10 |
| U. oligotricha | 2.11 | 3 |
| B. humidicola | 2.12 | 3 |
| U. panicoides | 2.14 | 3 |
| U. oligotricha | 2.15 | 1 |
| U. mosambicensis | 3.3 | 3 |
| B. humidicola | 4.9 | 2 |
| B. brizantha | 5.1 | 4 |
| B. decumbens | 7.1 | 1 |
| B. humidicola | 8.1 | 3 |
| B. humidicola | 9.2 | 3 |
| B. decumbens | 10.1 | 1 |
| U. mosambicensis | 11.1 | 1 |
| U. mosambicensis | 12.1 | 5 |
| B. decumbens | 14.1 | 4 |
| B. humidicola | 15.2 | 3 |
| B. distachya | 8 | 2 |
| B. miliiformis | 26 | 3 |
| Total Isolates | | 97 |

Figure 2:
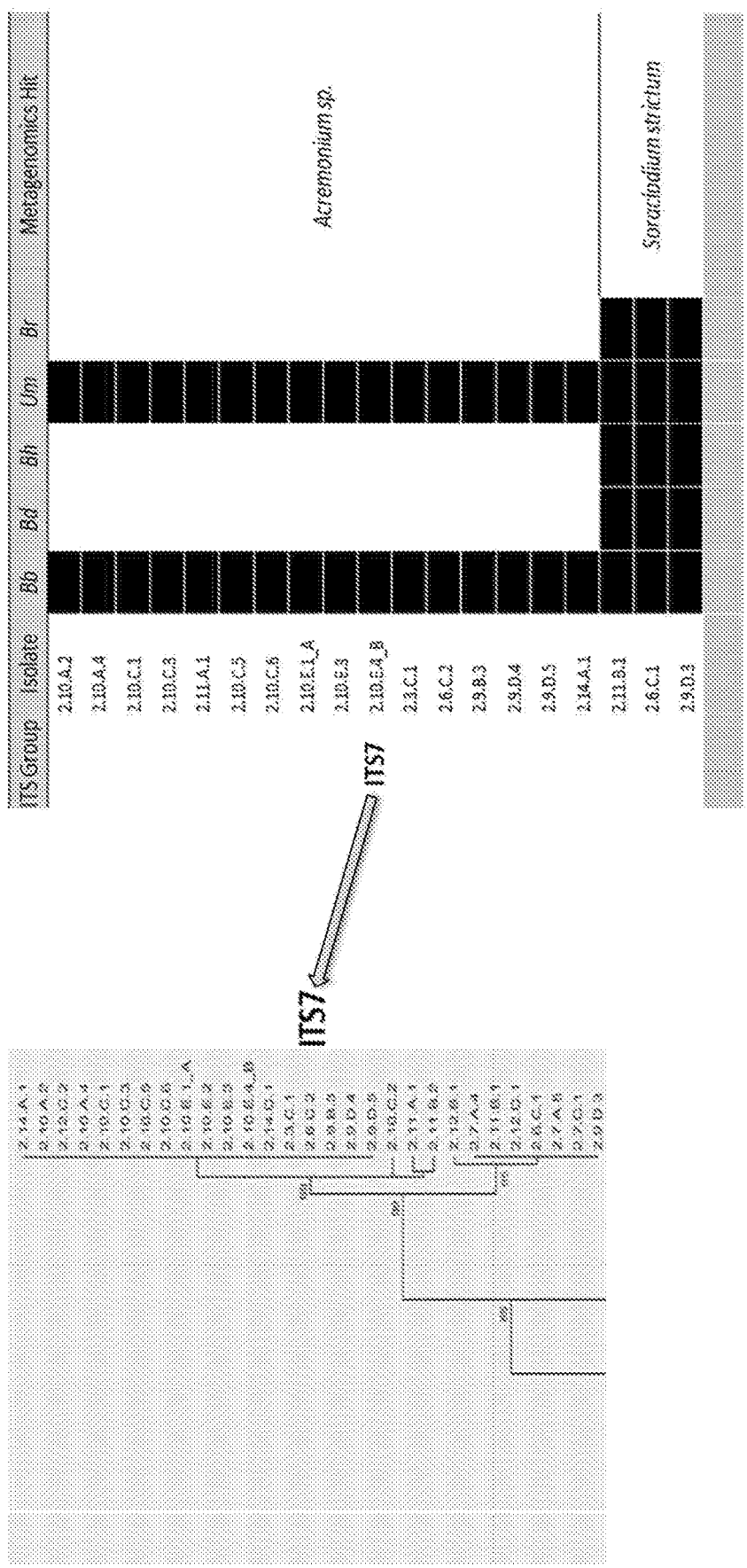
FIG. 2A is an enlarged bootstrap consensus tree of FIG. 2.
Figure 2:
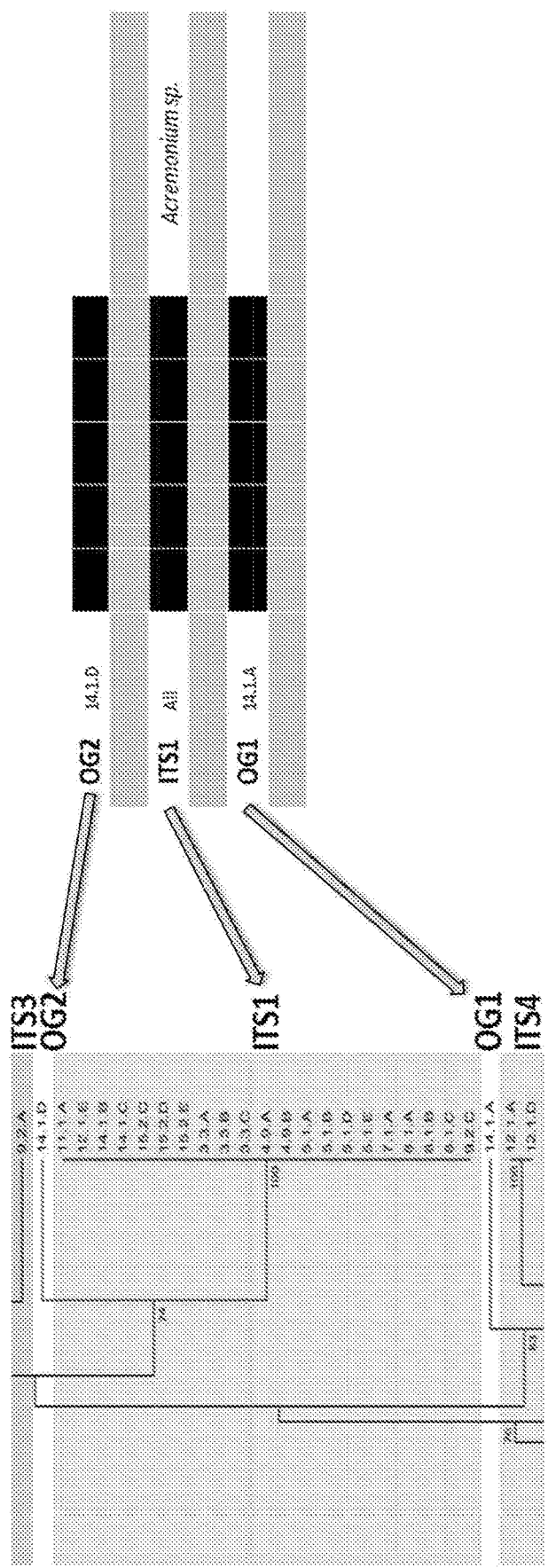
Figure 2:
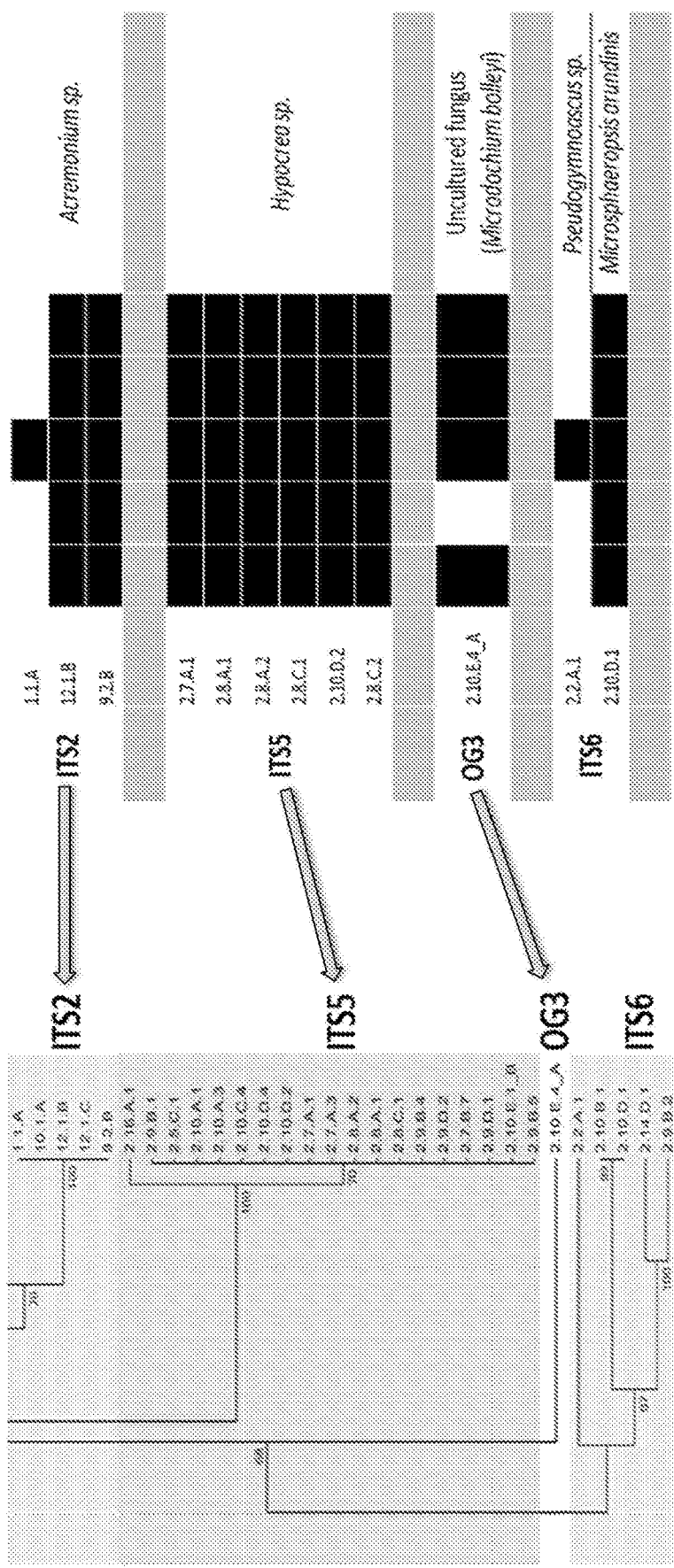
Figure 2A:
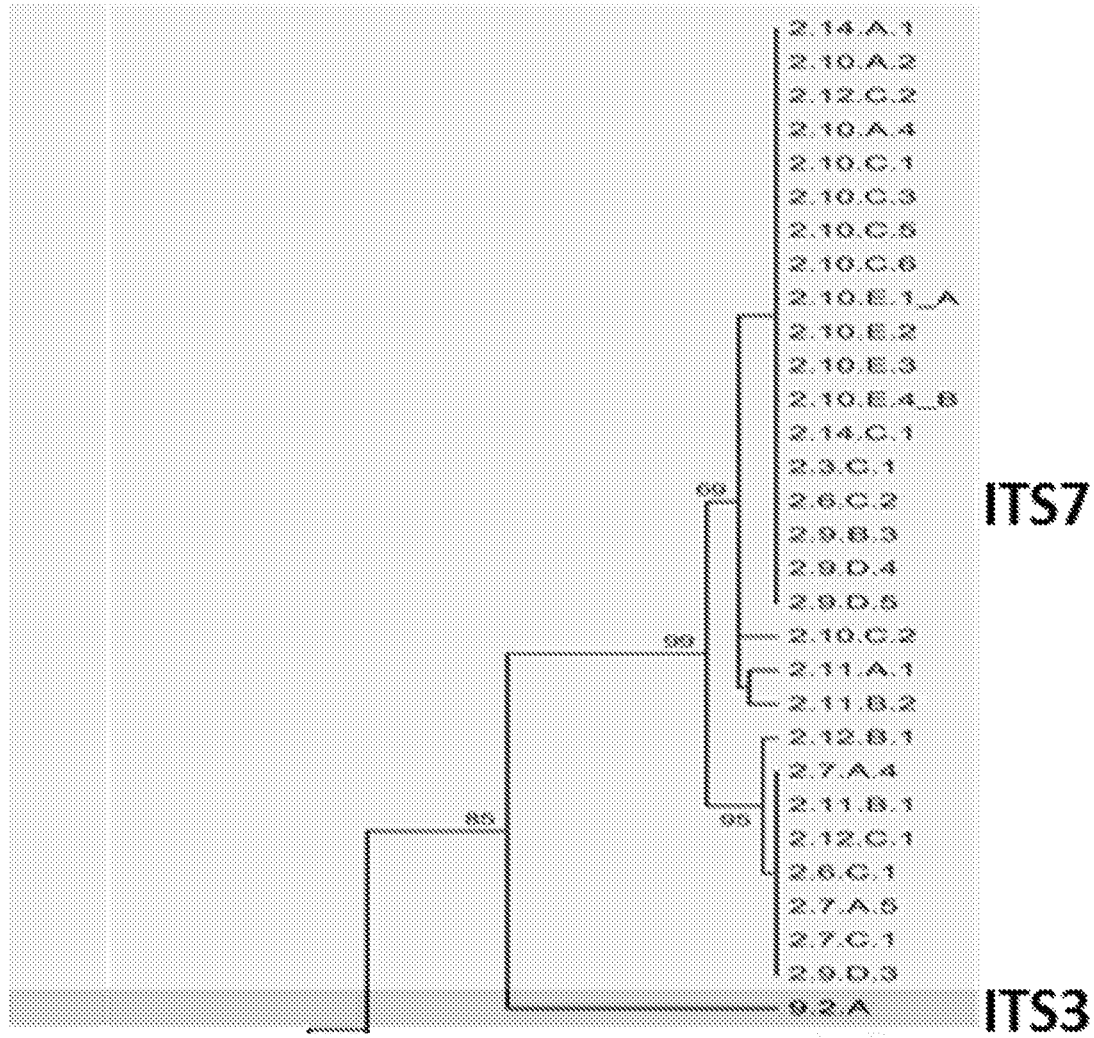
Figure 2A:
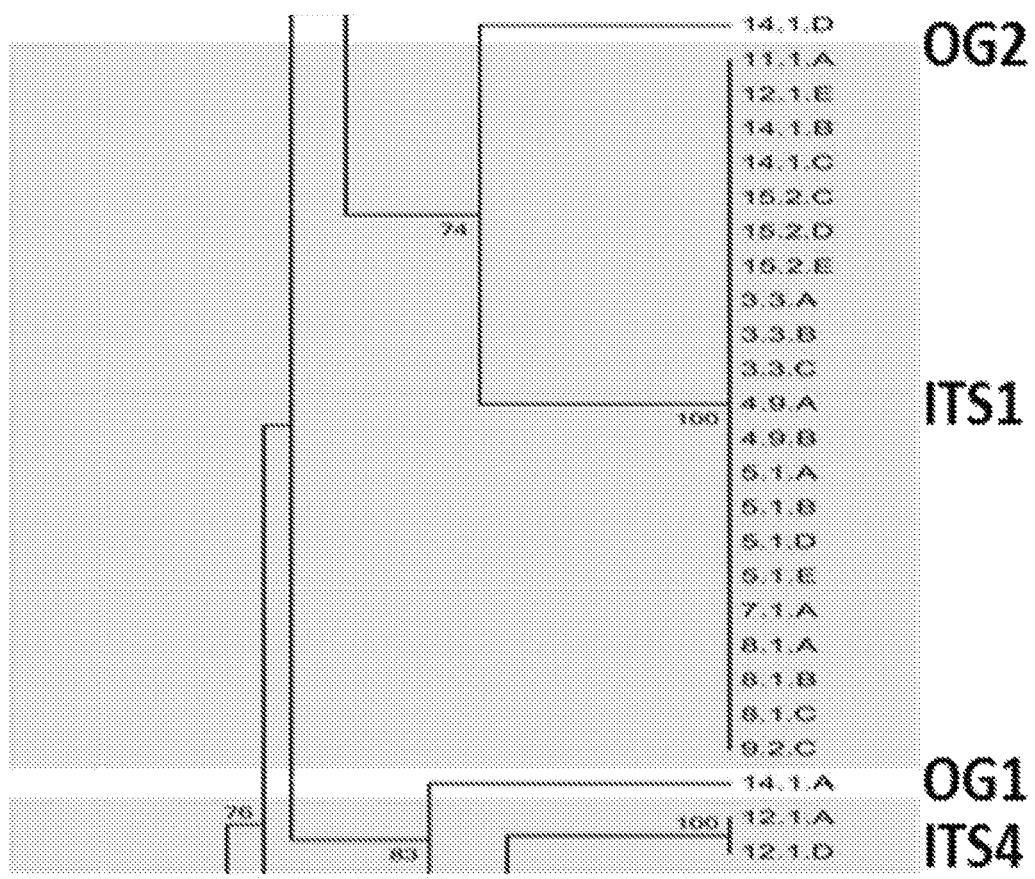
Figure 2A:
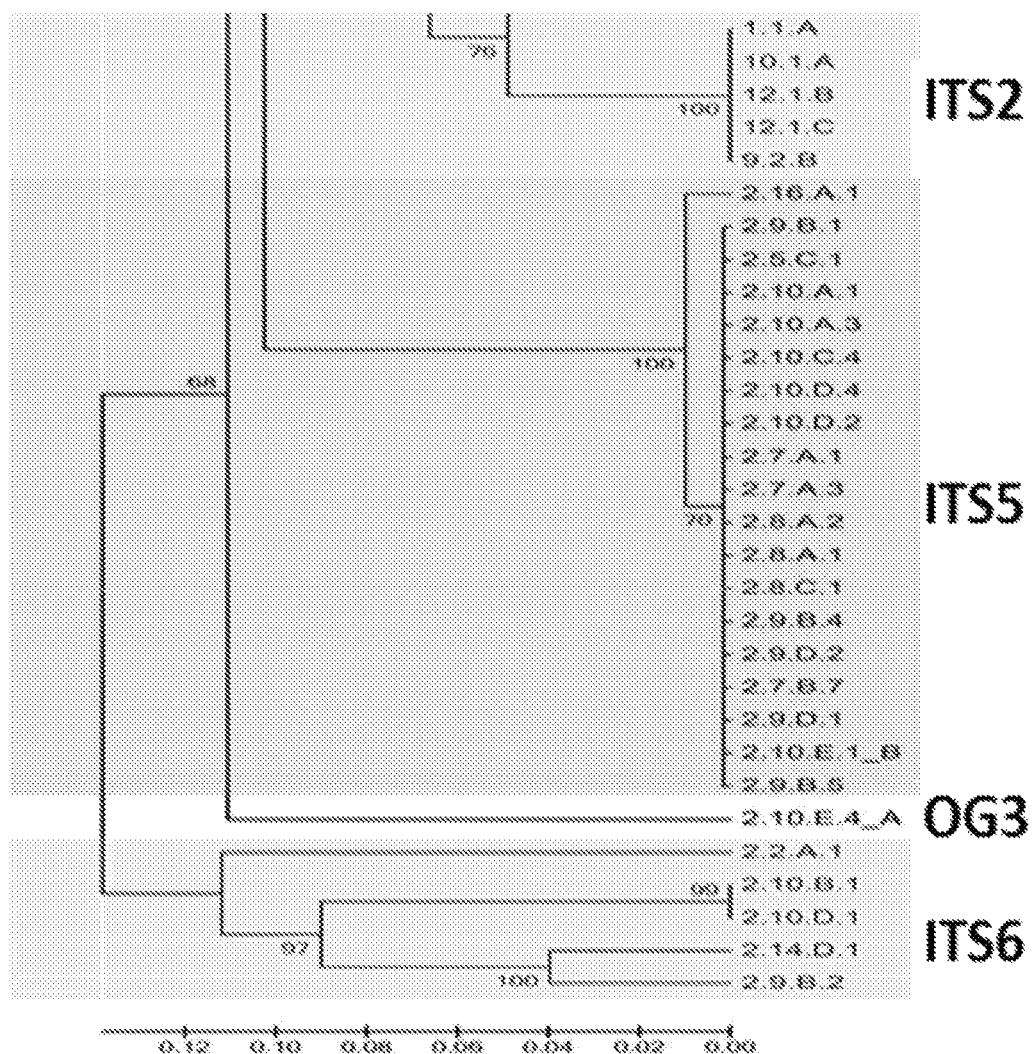

The rDNA-ITS region sequence for selected isolated and culturable fungal endophyte strains was used to identify their presence/absence in the microbiomes of 5 *Brachiaria-Urochola* species (Bb—*B. brizantha*; Bh—*B. humidicola*; Bd—*B. decumbens*; Um—*U. mosambicensis*; Ur—*U. ruziensis*) (FIGS. 2-2A). A total of 27 isolates had sequence homology (>10e-145) to OTUs in the metagenomics analysis, further validating their endophytic ecological niche. The isolates had sequence homology to *Acremonium* sp., *Sarocladium strictum*, *Hypocrea* sp., *Microsphaeropsis arundinis*, an uncultured fungal sp. and *Pseudogymnoascus* sp. The pattern observed for the presence of ITS across host species follows within ITS Group similarity. For example, ITS5 (for example 2.15.A.2) and ITS1 form single ITS groups (no within group sub-clustering) and appear to be present ubiquitously in *Brachiaria-Urochola*. In contrast, ITS7 shows patterns of host presence/absence that is related to the three ITS7 sub-clusters identified [represented by endophyte isolates 2.3.C.1 (cluster 1), 2.10.C.2 (cluster 2), 2.12.B.1 and 2.11.B.1 (cluster 3)]. The ITS6 group is genetically diverse, with three distinct clusters. Endophyte isolate 2.2.A.1 was detected in only 1 of 5 host species tested, while 2.10.D.1 shows a broad host range. The ITS2 Group endophytes exhibit two different host profiles. Endophytes 12.1.B and 9.2.B show a broad host range, being present in each of the 5 host species tested. In contrast 1.1.A shows a narrow host range, as it was detected in only 1 of 5 host species tested. Variation in host colonisation between putative sub-groups of the same taxonomic group may be an indicator of host-endophyte co-evolution and specialisation.

Example 3—Brachialactone is Microbial in Origin

Figure 3:
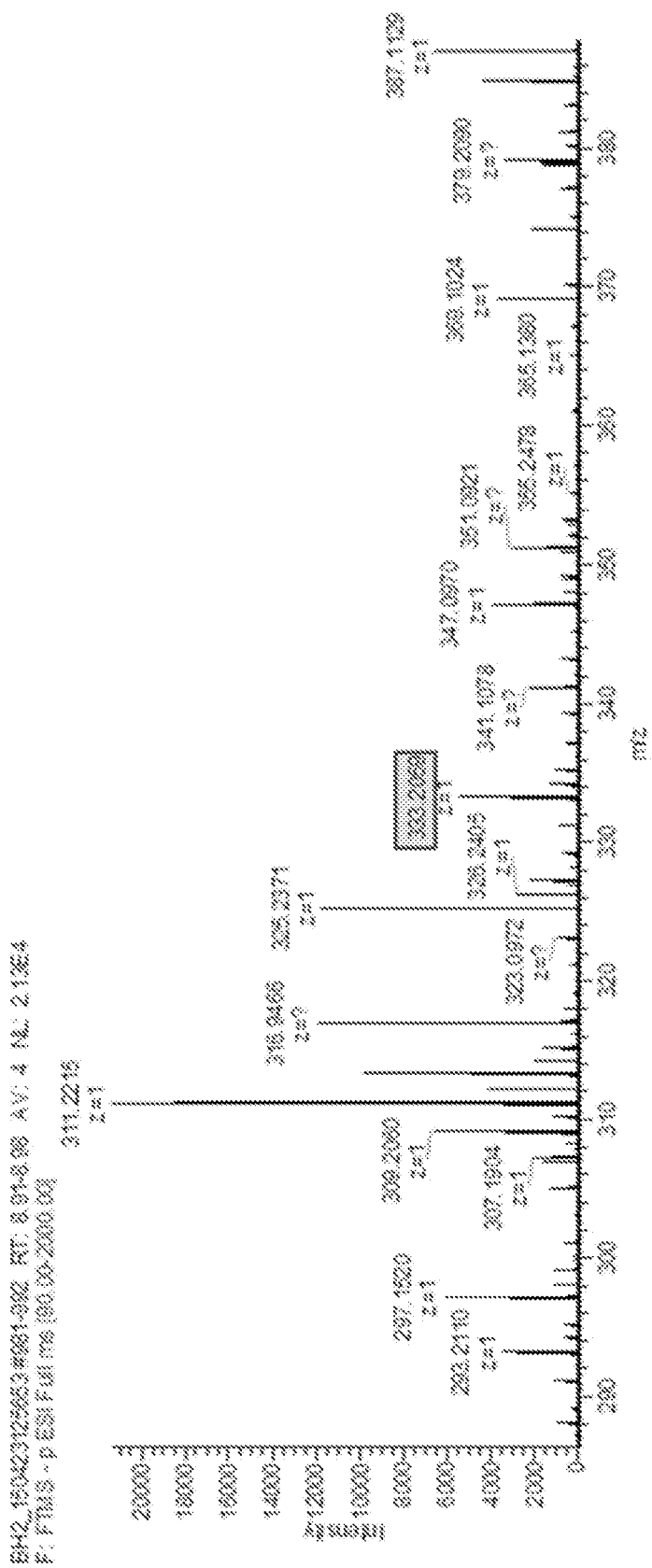
FIG. 3 shows an LC(ESI)-MS mass spectra identifying brachialactone, displaying extracted ion chromatogram at RT: 8.91-8.98 minutes.
Figure 4:
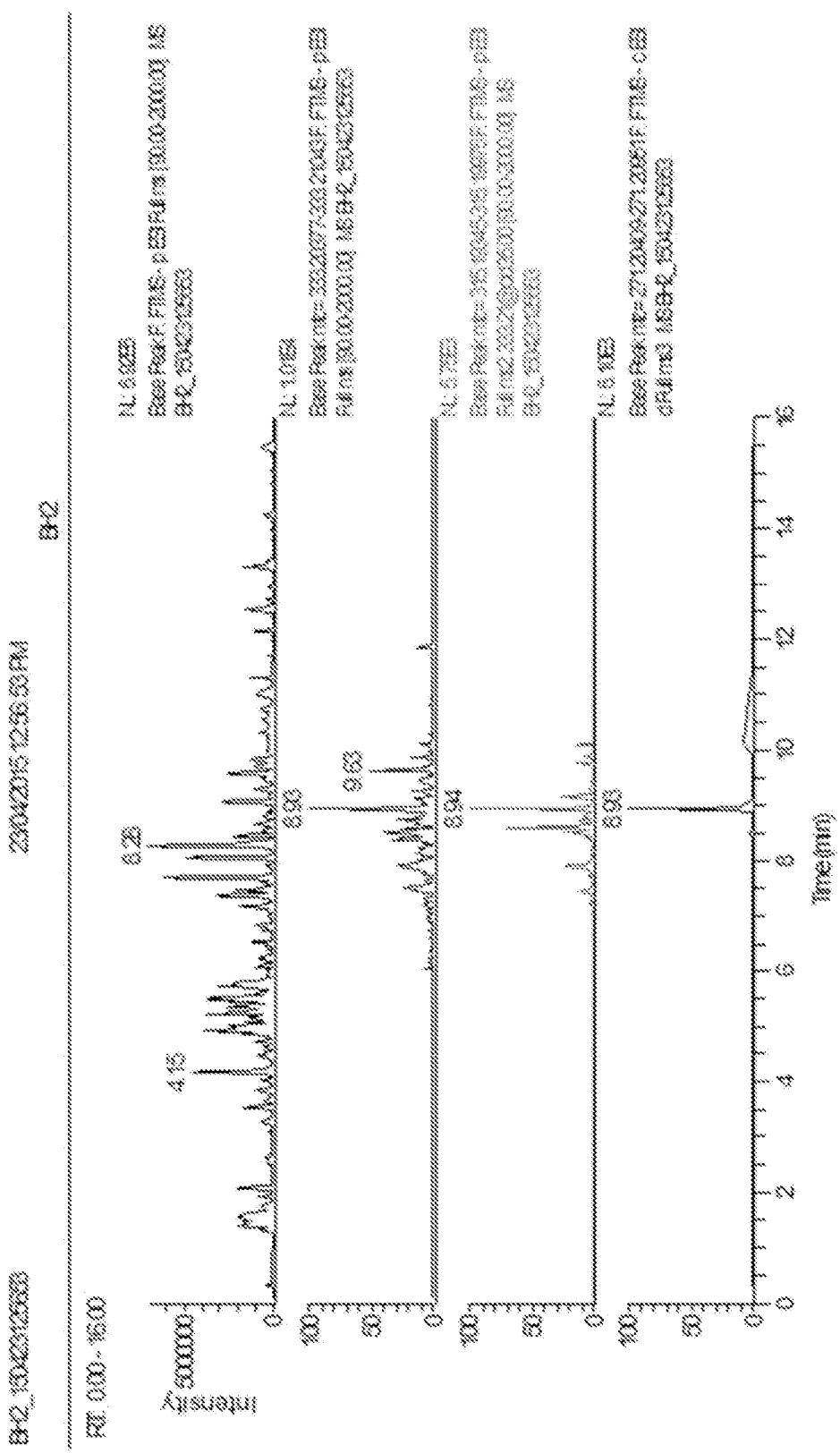
FIG. 4 shows MS fragmentation brachialactone fragments (333.2059, 315.1964, 271.2068) at RT 8.93 minutes of the LC(ESI)-MS mass spectra of FIG. 3.
Figure 5:
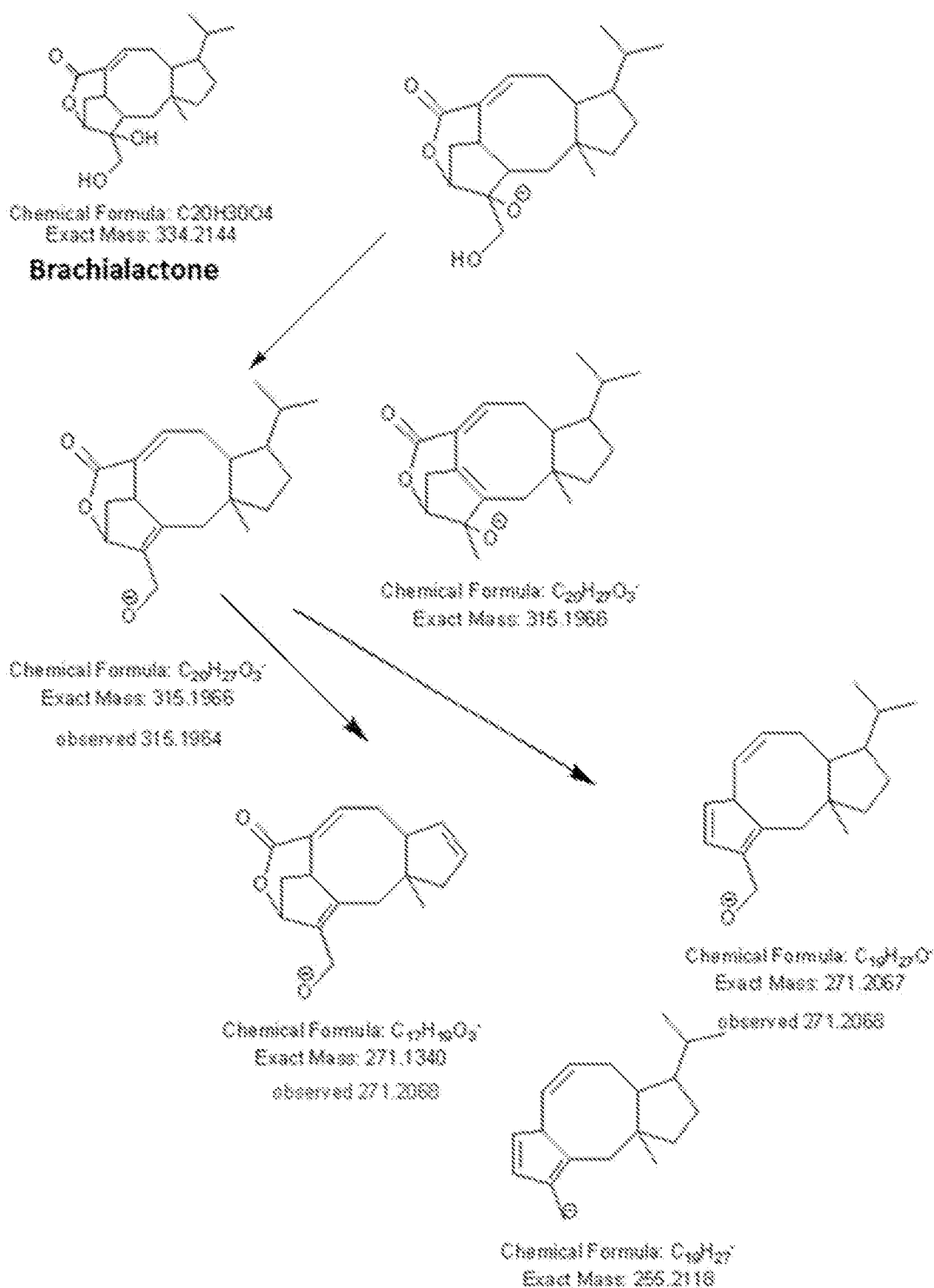
FIG. 5 shows the structure of brachialactone and the structures of the fragments responsible for the fragmentation of FIG. 4.

Mature plants of *Brachiaria-Urochloa* grass-endophyte associations that had been maintained in a controlled environment were subjected to metabolic profiling analysis. Four individual plants (biological replicates) from each of three *Brachiaria-Urochloa* species (*B. humidicola, U. mosambicensis, B. ruziensis*) were analysed for the presence of brachialactone using liquid chromatography-mass spectrometry (LC-MS). Freeze-dried pseudostem samples were prepared for LC-MS analysis using an 80% methanol extraction procedure. The compound brachialactone was identified in the root tissues of *brachiaria*-endophyte associations (*B. humidicola, B. ruziensis*) (FIGS. 3 to 5; Table 7). The presence of brachialactone was confirmed through MS (ions extracted at the mass to charge ratio [m/z] of 333.2059 at RT 8.93 minutes). Brachialactone was not detected in *B. decumbens*-endophyte associations or *U. mosambiciensis*-endophyte associations (Table 7).

TABLE 7

Brachialactone detection in *Brachiaria-Urochloa*. Samples of *B. humidicola*-endophyte and *B. ruziensis*-endophyte associations show presence of brachialactone.

| Brachiaria-Urochloa | Brachialactone |
| --- | --- |
| B. humidicola | + |
| U. mosambiciensis | − |
| B. decumbens | − |
| B. ruziensis | + |

+: brachialactone detected;
−: no brachialactone detected

Example 4—an Optimised Method for Inoculation of *Brachiaria* Endophytes into *Brachiaria-Urochola*

A host panel comprising commercially relevant *Brachiaria-Urochola* germplasm was established to enable inoculation of genetically novel and highly diverse endophyte isolates into a single host genotype. An optimised method for endophyte inoculation into host plants free of microbial organisms in axenic conditions was developed, facilitating a high frequency of successful inoculation (Table 8). Four fungal endophytes representing four of the rDNA sequence-defined clades were identified as candidates for inoculation and characterisation into the *Brachiaria-Urochola* host panel.

Sterilised *brachiaria* seed are germinated under aseptic conditions to remove microbial organisms from the host plants to be used for inoculation. Microbe-free donor plantlets are grown on shoot multiplication media (M3B) under sterile conditions. Donor shoots are split into single tillers and transferred to root multiplication media (MS+NAA).

Single tillers are grown for 2-3 weeks to promote root growth, plantlets are then again split into single tillers and the outer sheath is removed to reveal shoot initial. Shoot initials with intact roots are transferred to water agar for inoculation of endophyte mycelia. For endophyte inoculation, a small cut is made across the shoot meristem, and endophyte is inoculated into the wound. Following inoculation, plantlets are retained on ½ MS media for 2 weeks. They are then transferred to soil and grown under glasshouse conditions for 8 weeks before testing for endophyte presence using a diagnostic set of strain specific SSR markers (FIG. 6).

Endophyte inoculation frequency was determined for each candidate endophyte, approximately 6 months post inoculation, using a diagnostic (i.e. specific allele sizes at each SSR loci for each endophyte) set of simple sequence repeat (SSR) markers for each endophyte isolate.

Successful inoculation was achieved for representative endophytes from each of the ribosomal DNA sequence-defined clades (Table 8). Variation between endophyte isolates representing different ITS groups was observed. ITS5 (2.15.A.2)>ITS7 (2.10.C.2)>ITS2 (12.1.B)>ITS1 (5.1.B). Cross species compatibility was also observed. Endophyte isolate 2.15.A.2 (58 to 83%) and 2.10.C.2 (38% to 83%) exhibit broad species compatibility compared to the moderately compatible 12.1.B (8 to 76%) and narrow host compatibility of 5.1.B (0 to 7%). As would be expected, each endophyte strain shows highest inoculation frequency for the species from which it was originally isolated.

TABLE 8

Summary of inoculation frequencies (%). Data presented here is for stable *Brachiaria-Urochola* endophyte associations identified 3 to 6 months post inoculation. A diagnostic set of SSR markers specific for *Brachiaria-Urochola* endophytes are used to test for endophyte presence and identity in planta. Shown here is the percentage of endophyte positive plants identified from the total number of plants harvested. Host plant and endophyte averages are shown in columns highlighted in grey. The *Brachiaria-Urochola* species from which the endophyte was isolated is highlighted in light grey.

| Host Plant Species | Endophyte Isolate | | | | Host |
|---|---|---|---|---|---|
| | ITS 1 5.1.8 | ITS 2 12.1.B | ITS 5 2.15.A.2 | ITS 7 2.10.C.2 | Plant Average |
| Brachiaria brizantha | 7 | 24 | 58 | 43 | 33 |
| Brachiaria decumbens | 2 | 15 | 72 | 70 | 40 |
| Brachiaria humidicola | 3 | 42 | 83 | 38 | 41 |
| Urochloa mosambicensis | 0 | 76 | 80 | 83 | 60 |
| Brachiaria Hybrid | 0 | 8 | 62 | 61 | 33 |
| Endophyte Average | 2 | 33 | 71 | 59 | 41 |

Variation in inoculation ability of the host was also observed. *U. mosambicensis* forms stable associations with a broad range of fungal endophytes at a very high frequency of successful inoculation (60%). Also of note is that *U. mosambicensis* forms associations with multiple, highly diverse fungal endophytes (FIG. 1; Table 6). Endophyte strains representing 6 of the 7 ITS groups identified in brachiaria were isolated from this species (FIG. 1). *B. humidicola* forms stable associations with a broad range of fungal endophytes at a high frequency of successful inoculation (41%). As for *U. mosambicensis*, this species naturally harbours a diversity of multiple endophytes, with 4 of 7 ITS groups identified (FIG. 1).

Example 5—Metagenomics Analysis of the Brachiaria-Urochloa Seed Microbiome

A significant challenge in plant microbiome studies is that in order to analyse the endophytic component of a plant microbiome, it is necessary to extract DNA from plant tissues. The presence of a high proportion of plant DNA: microbe DNA (in the order of 20:1 for bacteria and 1:1 for fungi) in DNA extracted affects downstream sequence analysis. In previous studies, one way this has been dealt with is to generate large numbers of sequence reads to achieve a target number of microbiome reads.

In this example, a method was developed to enrich for the microbiome (both bacterial and fungal DNA) when extracting DNA from plant seed. The method is not limited in application to plant seed, and may be applied to any plant tissue from any species of interest, including leaf, stem and/or root plant material.

Seed-associated endophytic microbes are of interest as they may be exploited in a molecular breeding scenario whereby the microbe and host plant are co-selected for a particular trait of interest. Further, the presence of endophytic microbes in both root and seed microbiomes is of particular interest as seed associated microbes that are distributed throughout the plant may be associated with enhanced performance traits, such as pest and disease resistance, or biological nitrification inhibition (BNI) through the production of brachialactone.

Variation in host seed colonisation may be an indicator of host-endophyte co-evolution and specialisation Once isolated and purified, individual components of the endophytic seed microbiome can be genome sequenced and characterised for molecular marker development, taxonomic identification and phylogenomic analyses. Selected microbiome component organisms can also be phenotypically assessed singly and in combination to identify microbes that confer enhanced production traits, for example BNI, to a range of commercially significant *brachiaria* species. There is potential to further exploit the biological properties of the *brachiaria* microbiome across a broad range of crop species to the benefit of sustainable agriculture and the environment.

Example 6—Methodology for Enriching for Bacterial and Fungal DNA in Microbiome Analysis of Seed A method was developed to enrich for the microbiome (bacterial and fungal DNA) component in *brachiaria* seed (FIG. 7). Although used for plant seed in this example, the method may also be applied to any plant tissue from any species of interest. Depending on the plant tissue, the person skilled in the art would understand that small changes may be made to the method to optimise the enrichment of the microbiome, for example the amount of grinding of the plant material may be varied e.g. from finely ground to roughly ground, depending on the nature of the plant material.

Fifty grams of seed from each of the ten selected accessions (Table 9) was surface sterilised (5% [w/v] NaHCl and Tween 20) for 30 min with shaking. Seed samples were then rinsed eight to ten times in sterile MilliQ water to ensure the sterilant had been completely removed. Seed were dried on sterile filter paper under aseptic conditions overnight. Dried seeds were partially ground using a genogrinder (SPEX SamplePrep 2010 Geno/GrinderR, Metuchen, USA). Ground seeds were then washed twice for 12 hrs with absolute ethanol and continuous shaking. Following washes, samples were allowed to settle and the supernatant containing the seed associated endophytic microbiome collected. The supernatant was then completely evaporated under sterile conditions. DNA was extracted from the final crude (what was left following ethanol evaporation) using the Qiagen DNeasy plant mini kit according to manufacturer's instructions.

Simultaneously, DNA was also extracted from surface sterilised seeds (10 seeds from each accession) using the Qiagen DNeasy plant mini kit according to manufacturer's instructions. Bacteria and fungi were evaluated in the metagenomics analyses using the universal PCR primers 515f (Wang & Qian, 2009) and 806r (McBain et al, 2003) for profiling the bacterial microbiome (V4 region of the 16S rDNA gene, approx. 350 base pairs), and 58A2F (Martin & Rygiewicz, 2005) and ITS4 (White et al, 1990) for the fungal microbiome (ITS2 region of the rDNA genes, approx. 400 base pairs), with associated Illumina adapters. Ribosomal RNA gene amplicons were prepared and sequenced on the MiSeq (Illumina) according to the corresponding user guide.

TABLE 9

*Brachiaria* species used in this example.

| *Brachiaria* species | Records for BNI compound* production | Accessions used in this study Each accession refers to a different seed batch |
|---|---|---|
| B. brizantha | No | 5 |
| | | 59591 |
| B. humidicola | Yes | 2 |
| | | 4 |
| | | 8 |
| | | 9 |
| | | 15 |
| B. decumbens | Yes | 7 |
| | | 13 |
| B. ruziziensis | Yes | 30623 |

*BNI compound: Biological nitrification inhibition compounds e.g. brachialactone Example 7—Metagenomics Analysis to Identify the Seed Associated Endophytic Microbiome of *Brachiaria* Grasses The endophytic (bacterial and fungal) seed microbiomes of four selected *Brachiaria-Urochloa* species were profiled using metagenomics with the aim of identifying microbes associated with a particular species and or/trait, such as pest and disease resistance, or biological nitrification inhibition (BNI) through the production of brachialactone.

*Brachiaria* species examined included three species—*B. humidicola, B. ruziziensis, B. decumbens*—previously documented to produce biological nitrification inhibition (BNI) compounds, and *B. brizantha* which does not produce BNI compounds (Table 9).

The data is then analysed to identify the seed associated endophytic microbiome of *brachiaria*:
associated with the production of brachialactone
specifically with the BNI trait in *B. humidicola*
in general with the BNI trait (i.e. common to *B. humidicola, B. ruziziensis* and *B. decumbens*)
unique to *B. humidicola, B. ruziziensis, B. decumbens* or *B. brizantha*
in common to all *Brachiaria* species studied It is to be understood that various alterations, modifications and/or additions may be made without departing from the spirit of the present invention as outlined herein.

As used herein, except where the context requires otherwise, the term "comprise" and variations of the term, such as "comprising", "comprises" and "comprised", are not intended to be in any way limiting or to exclude further additives, components, integers or steps.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and/or regarded as relevant by a person skilled in the art.

REFERENCES 1. de Boer, A. H., & de Vries-van Leeuwen, I. J. "Fusicoccanes: diterpenes with surprising biological functions", *Trends in Plant Science*, 2012, 17(6), 360-368.
2. Subbarao, D. V., et al. "A bioluminescence assay to detect nitrification inhibitors released from plant roots: a case study with *Brachiaria humidicola*", *Plant Soil*, 2006, 288, 101-112.
3. Subbarao, G. V., et al. "Evidence for biological nitrification inhibition in *Brachiaria* pastures", *Proceedings of the National Academy of Sciences of the United States of America*, 2009, 106(41), 17302-17307.
4. White, T. J. et al. "Amplification and direct sequencing of fungal ribosomal RNA genes for phylogenetics", In PCR Protocols: A Guide to Methods and Applications, 1990, pp. 315-322, Academic Press.
5. Martin K J, Rygiewicz P T (2005) Fungal-specific PCR primers developed for analysis of the ITS region of environmental DNA extracts. *BMC Microbiology* 5: 28.
6. McBain A J, Bartolo R G, Catrenich C E, Charbonneau D, Ledder R G, Rickard A H, Symmons S A, Gilbert P (2003) Microbial characterization of biofilms in domestic drains and the establishment of stable biofilm microcosms. *Applied and Environmental Microbiology* 69: 177-185.
7. Wang Y, Qian P-Y (2009) Conservative fragments in bacterial 16S rRNA genes and primer design for 16S ribosomal DNA amplicons in metagenomic studies. *PloS one* 4: e7401.

The invention claimed is:

1. A method for selecting brachialactone compound producing fungal endophyte strains that confer a biological nitrification inhibition (BNI) trait to a plant of *Brachiaria-Urochoa* species complex, said method comprises the steps of:
 (a) providing samples of plant material from plant species of the *Brachiaria-Urochoa* species complex, wherein at least one of said plant species demonstrates the BNI trait by producing the brachialactone compound;
 (b) subjecting said samples to metagenomic analysis using universal PCR primers which are directed to ITS2 region of rDNA genes of said fungal endophyte strains to generate a sequence data;
 (c) identifying fungal operational taxonomic units (OTUs) in said samples, and in an ITS2 region of a reference fungal endophyte strain capable of delivering a BNI trait to a plant using said sequencing data;
 (d) comparing the OTUs present in said samples and in said reference to identify core microbiomes, supplemental microbiomes and unique microbiomes, to identify microbiomes associated with the BNI trait; and
 (e) selecting fungal endophyte strains containing said core microbiomes, supplemental microbiomes, and unique microbiomes associated with the BNI trait.

2. The method according to claim 1, wherein the plant species of the *Brachiaria-Urochoa* species complex is selected from the group consisting of *Brachiaria brizantha, Brachiaria decumbens, Brachiaria humidicola, Brachiaria stolonifera, Brachiaria ruziziensis, Urochloa brizantha, Urochloa decumbens, Urochloa humidicola, Urochloa mosambicensis, Brachiaria marlothii, Brachiaria nigropedata, Urochloa dictyoneura, Urochloa oligotricha, Urochloa panicoides, Brachiaria obtusiflora, Brachiaria serrifolia, Urochloa advena, Urochloa arrecta, Urochloa brachyura, Urochloa eminii Urochloa mollis, Urochloa xantholeuca, Urochloa oligotricha, Urochloa panicoides, Urochloa plantagima, Urochloa platynota, Urochloa xantholeuca, Brachiaria holosericea, Brachiaria reptans, Brachiaria milliformi* and *Brachiaria distachya*.

3. The method according to claim 1, wherein the samples of said plant material are selected from the group consisting of leaf, stem and root.

4. The method according to claim 1, wherein the step of providing samples of said plant material from said plant species of the *Brachiaria-Urochoa* species complex comprises the steps of:
(i) grinding said samples of plant material;
(ii) washing the ground plant material with an alcohol; and
(iii) extracting nucleic acid from the alcohol wash.

5. The method according to claim 1, wherein the identified endophyte is selected from the group consisting of *Hypocrea* sp./*Acremonium* sp. 2.15.A.2, *Acremonium* sp. 2.3.C.1, *Microsphaeropsis arundis* 2.10.D.1, *Sarocladium* sp./*Acremonium* sp. 2.12.B.1, *Sarocladium* sp./*Acremonium* sp. 2.10.C.2 and *Sarocladium* sp./*Acremonium* sp. 2.11.B.1, as deposited at the National Measurement Institute with accession numbers V15/028237, V15/028238, V15/028239, V15/028240, V15/028241 and V15/028242, respectively.

6. The method according to claim 1, wherein the plant species of the *Brachiaria-Urochoa* species complex is interspecific or intraspecific hybrids of *Brachiaria-Urochloa* species complex.

\* \* \* \* \*

UNITED STATES PATENT AND TRADEMARK OFFICE
CERTIFICATE OF CORRECTION

PATENT NO. : 11,191,249 B2
APPLICATION NO. : 15/762988
DATED : December 7, 2021
INVENTOR(S) : Spangenberg et al.

Page 1 of 1

It is certified that error appears in the above-identified patent and that said Letters Patent is hereby corrected as shown below:

In the Claims

Column 39 Claim 2, Line(s) 13 should read:
... chloa plantaginea, Urochloa platynota, Urochloa xantho- Signed and Sealed this
Eighth Day of February, 2022

Drew Hirshfeld
*Performing the Functions and Duties of the*
*Under Secretary of Commerce for Intellectual Property and*
*Director of the United States Patent and Trademark Office*